United States Patent
Larsen et al.

(10) Patent No.: US 11,220,479 B2
(45) Date of Patent: Jan. 11, 2022

(54) GLUCOSYLCERAMIDE SYNTHASE INHIBITORS AND THERAPEUTIC METHODS USING THE SAME

(71) Applicant: THE REGENTS OF THE UNIVERSITY OF MICHIGAN, Ann Arbor, MI (US)

(72) Inventors: Scott D. Larsen, South Lyon, MI (US); James A. Shayman, Ann Arbor, MI (US); Kim Hutchings, Dexter, MI (US); Neil Moss, Ridgefield, CT (US); Qin Jiang, Latham, NY (US); Nicholas Mayhew, Niskayuna, NY (US); Emily Freeman, Voorheesville, NY (US); Zohreh Sajjadi Hashemi, Frederick, MD (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/076,852

(22) Filed: Oct. 22, 2020

(65) Prior Publication Data
US 2021/0122712 A1 Apr. 29, 2021

Related U.S. Application Data

(60) Provisional application No. 62/924,959, filed on Oct. 23, 2019.

(51) Int. Cl.
| C07D 205/04 | (2006.01) |
| C07D 207/09 | (2006.01) |
| C07D 405/12 | (2006.01) |

(52) U.S. Cl.
CPC ......... C07D 205/04 (2013.01); C07D 207/09 (2013.01); C07D 405/12 (2013.01)

(58) Field of Classification Search
CPC ... C07D 205/04; C07D 207/10; C07D 405/12
See application file for complete search history.

(56) References Cited

U.S. PATENT DOCUMENTS

| | | |
|---|---|---|
| 5,302,609 A | 4/1994 | Shayman et al. |
| 5,472,969 A | 12/1995 | Platt et al. |
| 5,525,616 A | 6/1996 | Platt et al. |
| 5,849,326 A | 12/1998 | Inokuchi et al. |
| 5,916,911 A | 6/1999 | Shayman et al. |
| 5,945,442 A | 8/1999 | Shayman et al. |
| 5,952,370 A | 9/1999 | Shayman et al. |
| 6,030,995 A | 2/2000 | Shayman et al. |
| 6,051,598 A | 4/2000 | Shayman et al. |
| 6,255,336 B1 | 7/2001 | Shayman et al. |
| 6,569,889 B2 | 5/2003 | Shayman et al. |
| 6,610,703 B1 | 8/2003 | Jacob et al. |
| 6,660,794 B2 | 12/2003 | Adedeji et al. |
| 6,855,830 B2 | 2/2005 | Hirth et al. |
| 6,916,802 B2 | 7/2005 | Shayman et al. |
| 7,196,205 B2 | 3/2007 | Siegel et al. |
| 7,253,185 B2 | 8/2007 | Shayman et al. |
| 7,615,573 B2 | 11/2009 | Siegel et al. |
| 10,202,340 B2 | 2/2019 | Larsen et al. |

FOREIGN PATENT DOCUMENTS

| | | |
|---|---|---|
| WO | WO-2008/150486 A2 | 12/2008 |
| WO | WO-2009/117150 A2 | 9/2009 |
| WO | WO-2010/014554 A1 | 2/2010 |
| WO | WO-2012/129084 A2 | 9/2012 |
| WO | WO-2016/126572 A2 | 8/2016 |

OTHER PUBLICATIONS

International Application No. PCT/US2020/056741, International Search Report and Written Opinion, dated Feb. 10, 2021.

Abe et al., Reduction of globotriaosylceramide in Fabry disease mice by substrate deprivation, J Clin Invest., 105(11):1563-1571 (2000).

Andersson et al., N-butyldeoxygalactonojirimycin: a more selective inhibitor of glycosphingolipid biosynthesis than N-butyldeoxynojirimycin, in vitro and in vivo, Biochem. Pharmacol., 59(7) 821-829 (2000).

Ashe et al., Iminosugar-based inhibitors of glucosylceramide synthase increase brain glycosphingolipids and survival in a mouse model of Sandhoff disease, PLoS One, 6(6):e21758 (2011).

Baek et al., Comparative analysis of brain lipids in mice, cats, and humans with Sandhoff disease, Lipids, 44(3):197-205 (2009).

Baek et al., N-butyldeoxygalactonojirimycin reduces brain ganglioside and GM2 content in neonatal Sandhoff disease mice, Neurochem. Int., 52(6): 1125-1133 (2008).

Barton et al., Replacement therapy for inherited enzyme deficiency— macrophage-targeted glucocerebrosidase for Gaucher's disease, N Engl J Med., 324:1464-1470 (1991).

Cecchelli et al., Modelling of the blood-brain barrier in drug discovery and development, Nat Rev Drug Discov 6: 650-661 (2007).

Denny et al., Influence of caloric restriction on motor behavior, longevity, and brain lipid composition in Sandhoff disease mice, J. Neurosci Res., 83(6):1028-1038 (2006).

Denny et al., Restricted ketogenic diet enhances the therapeutic action of N-butyldeoxynojirimycin towards brain GM2 accumulation in adult Sandhoff disease mice, J. Neurochem., 113(6):1525-1535 (2010).

Galjaard, Early diagnosis and prevention of genetic disease, Ann. Clin. Biochem. 16(6):343-353 (1979).

Garberg et al., In vitro models for the blood-brain barrier, Toxicol In Vitro, 19:299-334 (2005).

Hakomori, New directions in cancer therapy based on aberrant expression of glycosphingolipids: anti-adhesion and ortho-signaling therapy, Cancer Cells, 3(12):461-70 (1991).

(Continued)

Primary Examiner — Kamal A Saeed
(74) Attorney, Agent, or Firm — Marshall, Gerstein & Borun LLP

(57) ABSTRACT

Glucosylceramide synthase inhibitors and compositions containing the same are disclosed. Methods of using the glucosylceramide synthase inhibitors in the treatment of diseases and conditions wherein inhibition of glucosylceramide synthase provides a benefit, like Gaucher disease and Fabry disease, also are disclosed.

20 Claims, No Drawings

(56) References Cited

OTHER PUBLICATIONS

Hauser et al., Inheritance of lysosomal acid beta-galactosidase activity and gangliosides in crosses of DBA/2J and knockout mice, Biochem. Genet., 42(7-8) 241-257 (2004).

Inokuchi et al., Antitumor activity via inhibition of glycosphingolipid biosynthesis, Cancer Lett., 38(1-2):23-30 (1987).

Inokuchi et al., Inhibition of experimental metastasis of murine Lewis lung carcinoma by an inhibitor of glucosylceramide synthase and its possible mechanism of action, Cancer Res., 50(20):6731-7 (1990).

Jeyakumar et al., Central nervous system inflammation is a hallmark of pathogenesis in mouse models of GM1 and GM2 gangliosidosis, Brain, 126(Pt 4): 974-987 (2003).

Jeyakumar et al., Enhanced survival in Sandhoff disease mice receiving a combination of substrate deprivation therapy and bone marrow transplantation, Blood, 97(1) 327-329 (2001).

Jeyakumar et al., Neuropathology and applied neurobiology, vol. 28, No. 5, pp. 343-357 (2002).

Jimbo et al., Development of a new inhibitor of glucosylceramide synthase, J Biochem-Tokyo 127, 485-491 (2000).

Kasperzyk et al., N-butyldeoxygalactonojirimycin reduces neonatal brain ganglioside content in a mouse model of GM1 gangliosidosis, J. Neurochem., 89(3):645-653 (2004).

Kasperzyk et al., Substrate reduction reduces gangliosides in postnatal cerebrum-brainstem and cerebellum in GM1 gangliosidosis mice, J. Lipid Res., 46(4): 744-751 (2005).

Kolter et al., Sphingolipid metabolism diseases, Biochimica et Biophysica Acta, 1758(12): 2057-2079 (2006).

Kyrkanides et al., Peripheral blood mononuclear cell infiltration and neuroinflammation in the HexB-/-mouse model of neurodegeneration, J. Neuroimmunol. 203(1):50-57 (2008).

Leeson et al., Time-related differences in the physical property profiles of oral drugs, J Med Chem., 47: 6338-6348 (2004).

Lipinski et al., Exoerimental and computational approaches to estimate solubility and permeability in drug discovery and development settings, Advanced Drug Delivery Reviews 23, 3-25 (1997).

Liu et al., A genetic model of substrate deprivation therapy for a glycosphingolipid storage disorder, J. Clin. Invest., 103:497-505 (1999).

Lukina et al., Improvement in hematological, visceral, and skeletal manifestations of Gaucher disease type 1 with oral eliglustat tartrate (Genz-112638) treatment: 2-year results of a phase 2 study, Blood, 116(20):4095-8 (2010).

Lundquist et al., Prediction of drug transport through the bloodbrain barrier in vivo: a comparison between two in vitro cell models, Pharm. Res., 19:976-981 (2002).

Ma et al., Asymmetric dipolar cycloaddition reactions: a practical, convergent synthesis of chiral pyrrolidines, Tetrahedron:Asymmetry, 8(6):883-7 (1997).

Macala et al., Analysis of brain lipids by high performance thinlayer chromatography and densitometry, J. Lipid Res., 24(9):1243-1250 (1983).

Mahar Doan et al., Passive permeability and P-glycoproteinmediated efflux differentiate central nervous system (CNS) and non-CNS marketed drugs, J. Pharmacol. Exp. Ther., 303:1029-1037 (2002).

Mazzulli et al., Gaucher disease glucocerebrosidase and a-synuclein form a bidirectional pathogenic loop in synucleinopathies, Cell, 146(1):37-52 (2011).

Natoli et al., Inhibition of glucosylceramide accumulation results in effective blockade of polycystic kidney disease in mouse models, Nat. Med., 16(7):788-92 (2010).

Pajouhesh et al., Medicinal chemical properties of successful central nervous system drugs, NeuroRx, 2, 541-553 (2005).

Phaneuf et al., Dramatically different phenotypes in mouse models of human Tay-Sachs and Sandhoff diseases, Hum. Mol. Genet., 5(1):1-14 (1996).

Radin, Treatment of Gaucher disease with an enzyme inhibitor, Glycoconj J., 13(2):153-157 (1996).

Sango et al., Mouse models of Tay-Sachs and Sandhoff diseases differ in neurologic phenotype and ganglioside metabolism, Nature Genetics, 11(2):170-176 (1995).

Seyfried et al., Genetic variability for regional brain gangliosides in five strains of young mice, Biochem. Genet., 17(1-2): 43-55 (1979).

Seyfried et al., Heterosis for brain myelin content in mice, Biochem. Genet., 18(11-12):1229-1237 (1980).

Shayman et al., Glucosylceramide synthase: assay and properties, Methods Enzymol.,311:42-49 (2000).

Shayman et al., Inhibitors of glucosylceramide synthase, Methods Enzymol., 311:373-387 (2000).

Shayman, Eliglustat tartrate. Glucosylceramide synthase inhibitor, Treatment of type 1 Gaucher disease, Drugs of the Future 35, 613-621 (2010).

Shu et al., Role of PEPT2 in peptide/mimetic trafficking at the blood-cerebrospinal fluid barrier: studies in rat choroid plexus epithelial cells in primary culture, J.Pharmacol. Exp. Ther., 301: 820-829 (2002).

Shu et al., Src kinase mediates the regulation of phospholipase C-gamma activity by glycosphingolipids, J Biol Chem., 278:31419-31425 (2003).

Svensson et al., Epithelial glucosphingolipid expression as a determinant of bacterial adherence and cytokine production, Infect. Immun., 62(10):4404-10 (1994).

Wang et al., Evaluation of the MDR-MDCK cell line as a permeability screen for the blood-brain barrier, Int. J. Pharm., 288:349-359 (2005).

Weinreb et al., Guidance on the use of miglustat for treating patients with type 1 Gaucher disease, Am. J. Hematol., 80:223-229 (2005).

Wishart et al., DrugBank: a knowledgebase for drugs, drug actions and drug targets, Nucleic Acids Res., 36:D901-906 (2008).

Ziche et al., Angiogenesis can be stimulated or repressed in vivo by a change in GM3:GD3 ganglioside ratio, Lab Invest., 67(6):711-5 (1992).

GLUCOSYLCERAMIDE SYNTHASE INHIBITORS AND THERAPEUTIC METHODS USING THE SAME

CROSS-REFERENCE TO RELATED APPLICATION

This application claims the benefit of 62/924,959 filed Oct. 23, 2019, incorporated herein by reference in its entirety.

GOVERNMENT FUNDING

This invention was made with government support under NS092981 awarded by the National Institutes of Health. The government has certain rights in the invention.

FIELD OF THE INVENTION

The present invention relates to glucosylceramide synthase (GCS) inhibitors and to therapeutic methods of treating conditions and diseases wherein inhibition of GCS provides a benefit.

BACKGROUND OF THE INVENTION

Lysosomal storage diseases (LSDs), such as Gaucher disease and Fabry disease, occur when glycolipids accumulate in lysosomes due to defect in their catabolism. Two general strategies exist for the treatment of lysosomal storage diseases. The first strategy includes replacement or restoration of the defective or absent catabolizing enzyme (e.g., the infusion of recombinant enzyme, chaperone therapy, bone marrow transplantation, or gene therapy) (1). Enzyme replacement therapy is clinically approved for lysosomal storage diseases with peripheral manifestations, but is limited by the inability of the infused recombinant enzyme to distribute into the CNS, and by the frequent development of auto-antibodies to the protein in patients carrying null mutations.

The second strategy involves synthesis inhibition therapy focused on identifying small molecule inhibitors of GCS (2). Various classes of GCS inhibitors have been described, including imino sugars and analogues of D-threo-1-phenyl-2-decanoylamino-3-morpholino-propanol (PDMP) (3). The imino sugar N-butyldeoxynojirimycin (NBDNJ) is limited by its micromolar level inhibitory activity and limited specificity against the synthase. The limited specificity is associated with a high level of undesired effects resulting from secondary sites of action unrelated to glycolipid synthesis inhibition. These effects most notably include diarrhea, weight loss, and tremor, which limits the approved use of NBDNJ in the United States (4). One advantage of NBDNJ over PDMP-based homologs reported to date is its ability to distribute into the CNS. However, a recent study raised questions with respect to the ability of NBDNJ to lower CNS glycolipid levels (K. M. Ashe et al., Plos One 6:e21758 (2011)).

A number of GCS inhibitors have been disclosed, for example, in U.S. Pat. Nos. 5,302,609; 5,472,969; 5,525,616; 5,916,911; 5,945,442; 5,952,370; 6,030,995; 6,051,598; 6,255,336; 6,569,889; 6,610,703; 6,660,794; 6,855,830; 6,916,802; 7,253,185; 7,196,205; 7,615,573, and 10,202,340. Additional GCS inhibitors and treatments are disclosed in WO 2008/150486; WO 2009/117150; WO 2010/014554; and WO 2012/129084.

A compound structurally related to PDMP is N-((1R,2R)-1-(2,3-dihydrobenzo[b][1,4]dioxin-6-yl)-1-hydroxy-3-(pyrrolidin-1-yl)propan-2-yl)octanamide, also known as Genz-112638 and eliglustat tartrate (5). Phase 2 clinical trials using this drug for type 1 Gaucher disease demonstrated an efficacy equal to or greater than that for recombinant β-glucocerebrosidase, as evidenced by reversal of spleen and liver enlargement, correction of anemia, and improvements in thrombocytopenia and bone density (6). Phase 3 trials with eliglustat tartrate have been published, and eliglustat tartrate has been approved worldwide for Gaucher disease type 1 (7).

GSC inhibition also is expected to treat six other lysosomal storage diseases with CNS involvement, including early and late onset Tay-Sachs disease, Sandhoff disease, GM1 gangliosidosis, and types 2 and 3 Gaucher disease. For example, an experimental model of genetic epistasis demonstrated markedly improved survival in a mouse model of Sandhoff disease that also lack GM2 synthase (8). However, drug distribution studies indicate that eliglustat tartrate is not transported across the blood brain barrier (BBB) (5). A possible basis for the poor brain distribution of eliglustat tartrate may be that the drug is a substrate for the p-glycoprotein (MDR1) transporter, resulting in efflux of the drug.

Compounds that inhibit GCS have the potential to treat conditions associated with glycolipid accumulation. However, present day GCS inhibitors are limited by poor CNS penetration and/or low activity. An important advance in the art would be the discovery of GCS inhibitors, and particularly GCS inhibitors capable of crossing the BBB, that are useful in the treatment of diseases wherein GCS inhibition provides a benefit, such as type I, II, or III Gaucher disease, Fabry disease, Tay-Sachs disease, Sandhoff disease, diabetes, lupus, and other diseases and conditions associated with glycolipid accumulation in lysosomes. Accordingly, a need still exists in the art for efficacious compounds, compositions, and methods useful in the treatment of such diseases, alone or in conjunction with other therapies used to treat these diseases and conditions. The present invention is directed to meeting this need.

SUMMARY OF THE INVENTION

The present invention is directed to inhibitors of GCS, to methods of preparing the GCS inhibitors, to compositions comprising the inhibitors, and to methods of using the inhibitors in a therapeutic treatment of conditions and diseases wherein inhibition of GCS provides a benefit. The present compounds are potent inhibitors of GCS, and in some embodiments are capable of crossing the BBB.

More particularly, the present invention is directed to compounds having a structural formula (I):

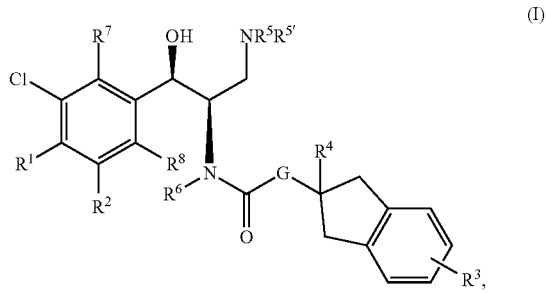

wherein $R^1$ and $R^2$, independently, are H, $C_{1-4}$alkyl, $OC_{1-4}$alkyl, $C_{3-6}$cycloalkyl, or $OC_{3-6}$cycloalkyl, each optionally substituted with one or more F, wherein one carbon of a cycloalkyl group optionally is replaced by O, or $R^1$ and $R^2$ can be taken together to form an $OCH_2CH_2O$ ring with either carbon atom substituted by one or two $CH_3$;

$NR^5R^{5'}$ is selected from the group consisting of 1-pyrrolidinyl, 3-fluoro-1-pyrrolidinyl, and 1-azetidinyl;

$R^3$ is H or F;

G is $CH_2$ or O;

$R^4$ is H or $CH_3$;

$R^6$ is H, $C_{1-3}$alkyl, $C_{3-6}$cycloalkyl, or $CD_3$; and $R^7$ and $R^8$, independently, are H, F, or $OC_{1-3}$alkyl, or a pharmaceutically acceptable salt thereof.

In one embodiment, the present invention provides a method of treating a condition or disease of interest by administering a therapeutically effective amount of a compound of structural formula (I) to an individual in need thereof. The disease or condition, for example, Gaucher disease, Fabry disease, Sandhoff disease, Tay-Sachs disease, and Parkinson's disease, is treatable by inhibition of GCS.

In yet another embodiment, the present invention provides a method of treating a subject having type 2 diabetes comprising administering to the subject a therapeutically effective amount of a compound of structural formula (I).

A method of treating a subject having renal hypertrophy, hyperplasia associated with diabetic nephropathy, or autosomal dominate polycystic kidney disease (ADPKD) also is included in the invention. The method comprises administering to the subject a therapeutically effective amount of a compound of structural formula (I).

A method of decreasing plasma TNF-α in a subject in need thereof also is included in the present invention. Indications treatable by the compounds of structural formula (I) also include, but are not limited to, multiple myeloma (for depletion of glucosylsphinogosine) and inhibition of viral and bacterial illnesses, the latter including hemolytic uremic syndrome where depletion of the receptor for shiga toxin, i.e., globotriaosylceramide, may be depleted from vascular endothelial cells. The method comprises administering to the subject a therapeutically effective amount of a compound of structural formula (I).

A method of lowering blood glucose levels in a subject in need thereof also is included in the present invention. The method comprises administering to the subject a therapeutically effective amount of a compound of structural formula (I).

A method of decreasing glycated hemoglobin levels in a subject in need thereof also is included in the present invention. The method comprises administering to the subject a therapeutically effective amount of a compound of structural formula (I).

A method of inhibiting glucosylceramide synthase or lowering glycosphingolipid concentrations in a subject in need thereof also is included in the present invention. The method comprises administering to the subject a therapeutically effective amount of a compound of structural formula (I).

The present invention also is directed to a method of treating a glomerular disease selected from the group consisting of mesangial proliferative glomerulonephritis, collapsing glomerulopathy, proliferative lupus nephritis, crescentic glomerulonephritis, and membranous nephropathy in a subject, comprising administering to the subject a therapeutically effective amount of a compound of structural formula (I).

In another embodiment, the invention is directed to a method of treating lupus in a subject comprising administering to the subject a therapeutically effective amount of a compound of structural formula (I).

In yet another embodiment, in the treatment of the above disclosed diseases, a compound of structural formula (I) can be administered on the sole therapeutic agent or in combination with a second therapeutic agent known to treat the disease of interest.

Another embodiment of the present invention is to provide a composition comprising (a) a GCS inhibitor of structural formula (I) and (b) an excipient and/or pharmaceutically acceptable carrier useful in treating diseases or conditions wherein inhibition of GCS provides a benefit.

Another embodiment of the present invention is to utilize a composition comprising a compound of structural formula (I) and a second therapeutically active agent in a method of treating an individual for a disease or condition wherein inhibition of GCS provides a benefit.

In a further embodiment, the invention provides for use of a composition comprising a GCS inhibitor of structural formula (I) and an optional second therapeutic agent for the manufacture of a medicament for treating a disease or condition of interest, e.g., Gaucher disease or Fabry disease.

Still another embodiment of the present invention is to provide a kit for human pharmaceutical use comprising (a) a container, (b1) a packaged composition comprising a GCS inhibitor of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

The GCS inhibitor of structural formula (I) and the second therapeutic agent can be administered together as a single-unit dose or separately as multi-unit doses, wherein the GCS inhibitor of structural formula (I) is administered before the second therapeutic agent or vice versa. It is envisioned that one or more dose of a GCS inhibitor of structural formula (I) and/or one or more dose of a second therapeutic agent can be administered.

In one embodiment, a GCS inhibitor of structural formula (I) and a second therapeutic agent are administered simultaneously. In related embodiments, a GCS inhibitor of structural formula (I) and second therapeutic agent are administered from a single composition or from separate compositions. In a further embodiment, the GCS inhibitor of structural formula (I) and second therapeutic agent are administered sequentially. A GCS inhibitor of structural formula (I), as used in the present invention, can be administered in an amount of about 0.005 to about 500 milligrams per dose, about 0.05 to about 250 milligrams per dose, or about 0.5 to about 100 milligrams per dose.

Compounds of the invention inhibit GCS and are useful research tools for in vitro study of GCS and its role in biological process.

These and other novel aspects of the present invention will become apparent from the following detailed description of the present embodiments.

DETAILED DESCRIPTION OF THE PREFERRED EMBODIMENTS

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "GCS" as used herein means glucosylceramide synthase.

The term "a disease or condition wherein inhibition of GCS provides a benefit" pertains to a condition in which GCS, and/or an action of GCS, is important or necessary, e.g., for the onset, progress, expression of that disease or condition, or a disease or a condition which is known to be treated by a GCS inhibitor (such as eliglustat tartrate). An example of such a condition includes, but is not limited to, Gaucher disease and Fabry disease. One of ordinary skill in the art is readily able to determine whether a compound treats a disease or condition mediated by GCS, for example, by assays which conveniently can be used to assess the activity of particular compounds.

The term "second therapeutic agent" refers to a therapeutic agent different from a GCS inhibitor of structural formula (I) and that is known to treat the disease or condition of interest. In particular, a GCS inhibitor of structural formula (I) can be used to act in synergy with second therapeutic agents that increase the activity of beta-glucocerebrosidase. For example when Gaucher disease is the disease or condition of interest, the second therapeutic agent can be a known for the treatment of type (I) Gaucher disease or Fabry disease, like isofagamine, enzyme replacement therapy, or gene therapy for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a compound of structural formula (I) is an inhibitor of GCS and can be used in treating diseases and conditions wherein inhibition of GCS provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active agent(s) that is(are) sufficient, when administered by a method of the invention, to efficaciously deliver the active agent(s) for the treatment of condition or disease of interest to an individual in need thereof. In the case of a lysosomal storage disorder, the therapeutically effective amount of the agent may reduce (i.e., retard to some extent and preferably stop) unwanted glycolipid accumulation and/or relieve, to some extent, one or more of the symptoms associated with the disorder.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a GCS inhibitor of structural formula (I) can be administered at the same time or sequentially in any order at different points in time as a second therapeutic agent. A present GCS inhibitor and the second therapeutic agent can be administered separately, in any appropriate form and by any suitable route. When a present GCS inhibitor and the second therapeutic agent are not administered concurrently, it is understood that they can be administered in any order to a subject in need thereof.

For example, a present GCS inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a GCS inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Compounds that inhibit glycolipid synthesis are known. As such, these compounds can be used for treating diabetes and lysosomal storage diseases, such as Tay-Sachs disease, Sandhoff disease, Gaucher disease, and Fabry disease. However, to date, these compounds have been limited by low activity, poor CNS penetration, or both.

For example, glycolipid synthesis inhibition is the basis for the treatment of type 1 Gaucher disease by the glucosylceramide (GCS) inhibitor eliglustat tartrate. However, the use of eliglustat for the treatment of glycosphingolipid storage diseases with CNS manifestations is limited by the lack of brain penetration of this drug.

Phase 2 clinical data for eliglustat tartrate demonstrated a clinical response in type 1 Gaucher disease that is comparable to enzyme replacement therapy, as measured by reduction in spleen and liver volume, correction of anemia, and improvement in thrombocytopenia. The adverse effects observed with NBDNJ, including weight loss, diarrhea, and tremor, were not observed in this clinical trial, as well as in an extension study. These observations are consistent with the high specificity of eliglustat tartrate and its absence of CNS penetration. While the absence of eliglustat tartrate distribution into brain may be advantageous for glycosphingolipidoses without CNS manifestations, including type 1 Gaucher and Fabry diseases, the identification of compounds of structural formula (I) that cross the BBB is of therapeutic benefit for disorders such as GM2 gangliosidoses, Tay-Sachs, Sandhoff disease, and types 2 and 3 Gaucher disease, that exhibit CNS manifestations.

The GCS inhibitors of the present invention are novel and potent inhibitors of GCS, and therefore are useful in the treatment of diseases and conditions resulting from an unwanted accumulation of glycolipids, including Gaucher disease and type II diabetes. Also provided are methods of treating a subject having an unwanted accumulation of glycolipids comprising administering a therapeutically effective amount of a present compound to a subject in need of such treatment.

Also provided are methods of preventing the proliferation of unwanted glycolipid accumulation in a subject comprising the step of administering a therapeutically effective amount of a compound of structural formula (I) to a subject at risk of developing a condition characterized by unwanted glycolipid accumulation. In some embodiments, compounds of structural formula (I) are capable of crossing the BBB, therefore are useful in the treatment of lysosomal storage diseases that previously could not be treated by a GCS inhibitor, for example, type II and type III Gaucher disease.

More particularly, the present invention is directed to compounds having a structural formula (I):

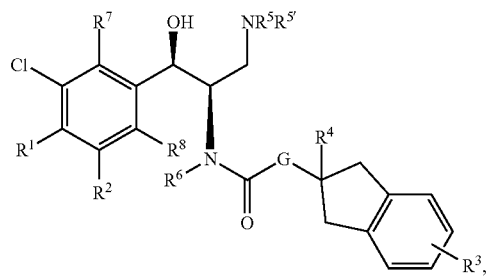

wherein $R^1$ and $R^2$, independently, are H, $C_{1-4}$alkyl, $OC_{1-4}$alkyl, $C_{3-6}$cycloalkyl, or $OC_{3-6}$cycloalkyl, each optionally substituted with one or more F, wherein one carbon of a cycloalkyl group optionally is replaced by O, or $R^1$ and $R^2$ can be taken together to form an $OCH_2CH_2O$ ring with either carbon atom substituted by one or two $CH_3$;

$NR^5R^{5'}$ is selected from the group consisting of 1-pyrrolidinyl, 3-fluoro-1-pyrrolidinyl, and 1-azetidinyl;

$R^3$ is H or F;

G is $CH_2$ or O;

$R^4$ is H or $CH_3$;

$R^6$ is H, $C_{1-3}$alkyl, $C_{3-6}$cycloalkyl, or $CD_3$; and $R^7$ and $R^8$, independently, are H, F, or $OC_{1-3}$alkyl, or a pharmaceutically acceptable salt thereof.

The compounds of structural formula (I) are used in methods of treating a disease or condition wherein inhibition of GCS provides a benefit, for example Gaucher disease, Fabry disease, Tay-Sachs disease, Sandhoff disease, diabetes, hypertrophy or hyperplasia associated with diabetic neuropathy, lupus, increased plasma TNF-α, elevated glycated hemoglobin levels, and a glomerular disease. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof. Such diseases and conditions include, but are not limited to, Parkinson disease, multiple myeloma, and ADPKD.

As used herein, the term "$C_{1-4}$alkyl" refers to straight chained and branched saturated hydrocarbon groups, non-limiting examples of which include methyl, ethyl, straight chain and branched propyl groups, and straight chain and branched butyl groups.

The term "$C_{3-6}$ cycloalkyl" refers to saturated cycloalkyl groups containing 3 to 6 carbon atoms, including cyclopropyl, cyclobutyl, cyclopentyl, and cyclohexyl. In some embodiments a —$CH_2$— of a cycloalkyl group is replaced by an oxygen atom.

The $C_{1-4}$alkyl and $C_{3-6}$cycloalkyl groups can be substituted with one or more F.

In various embodiments, $R^1$ is —H, —$OC(CH_3)_3$, —$OCH_3$, —$OCF_3$, —$OCHF_2$,

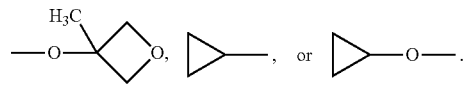

In another embodiment, $R^2$ is H.

In another embodiment, $R^1$ and $R^2$ are taken together to form

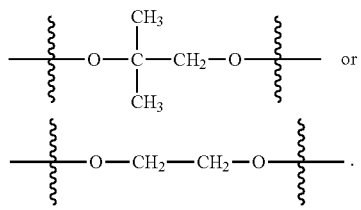

In one preferred embodiment, $R^3$ is H or F.

In another preferred embodiment, $R^4$ is H or $CH_3$.

In another preferred embodiment, one of $R^7$ and $R^8$ is H and the other is $OCH_3$.

In another preferred embodiment, —$NR^5R^{5'}$ is

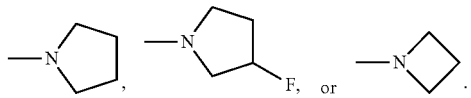

In various embodiments,

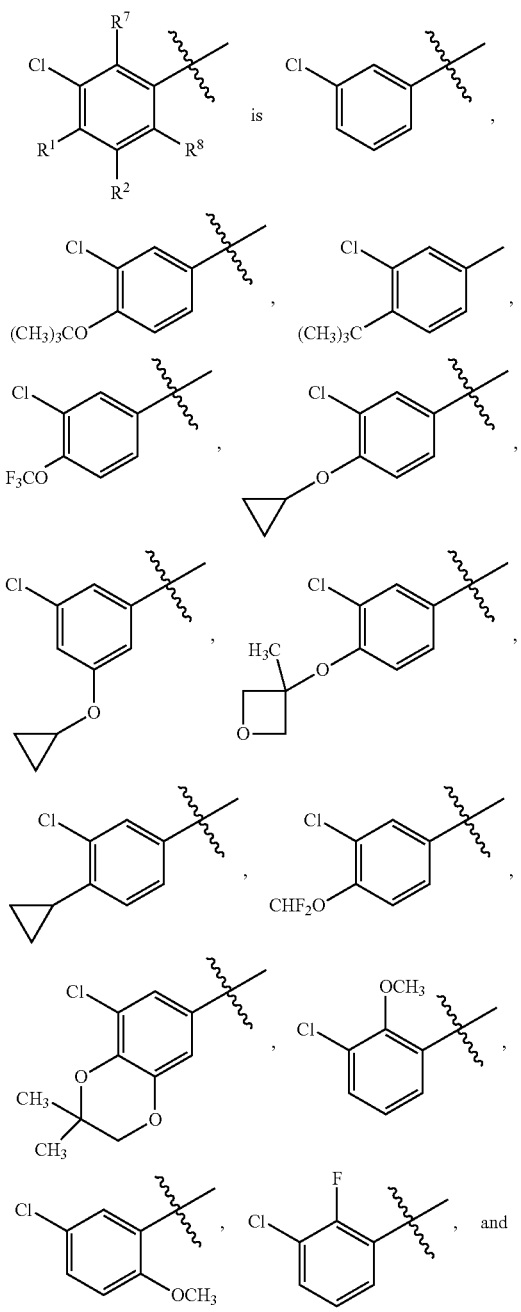

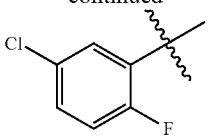

Additionally, salts, hydrates and solvates of the present compounds also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Compounds of the invention can exist as salts. Pharmaceutically acceptable salts of the compounds of the invention often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerophosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, glutarate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) as well as pharmaceutically acceptable salts, hydrates, or solvates thereof.

Some specific embodiments of the present invention include, but are not limited to:
Ex. 1
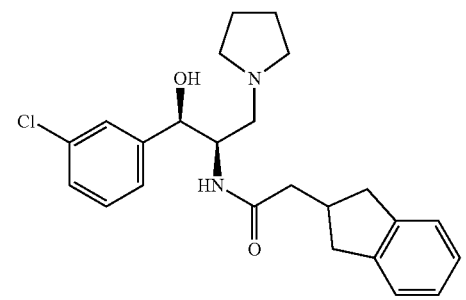
Ex. 2
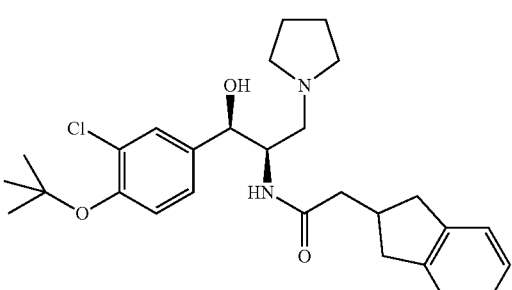
Ex. 3
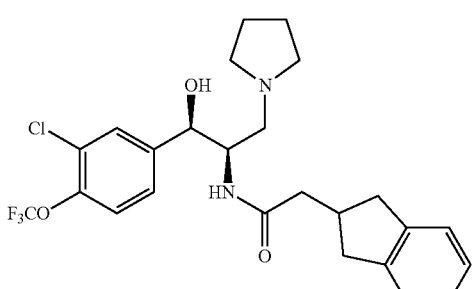
Ex. 4
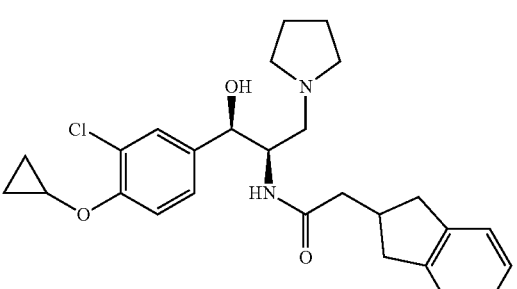
Ex. 5
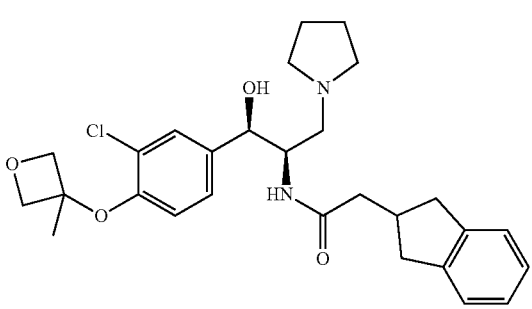
Ex. 6
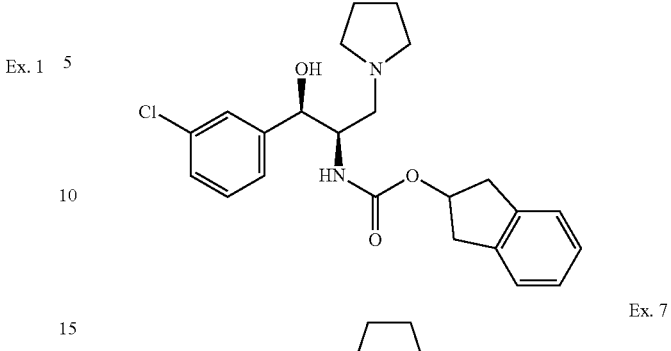
Ex. 7
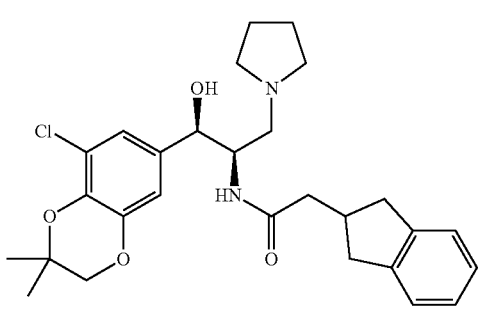
Ex. 8
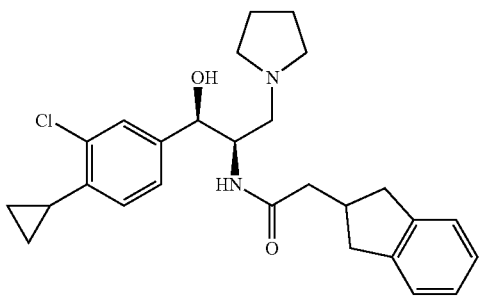
Ex. 9
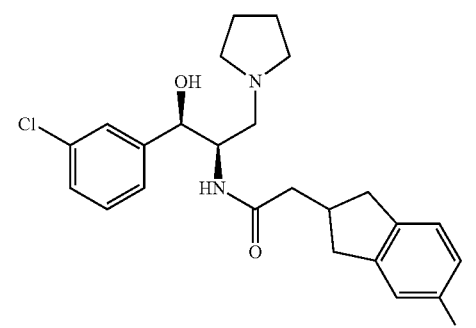
Ex. 10
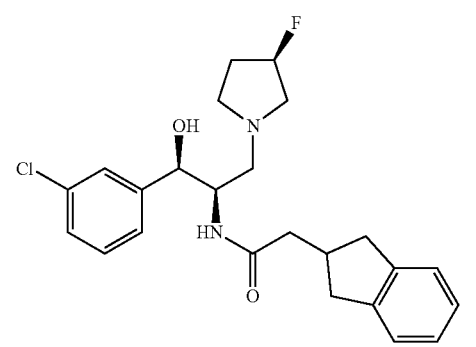

Ex. 11
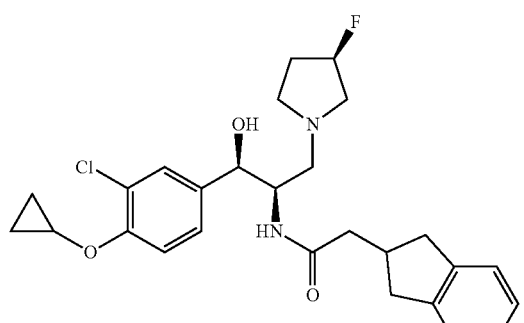
Ex. 12
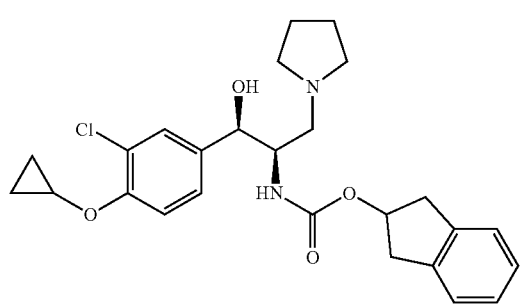
Ex. 13
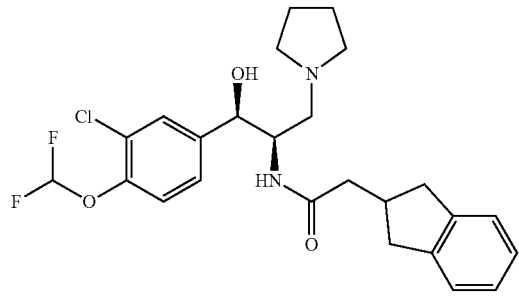
Ex. 14
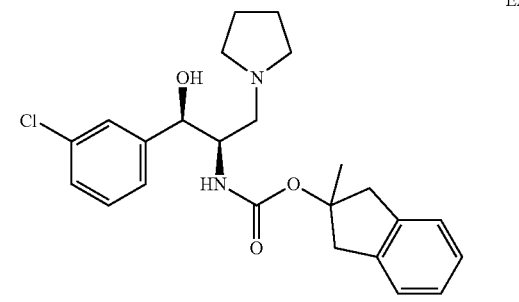
Ex. 15
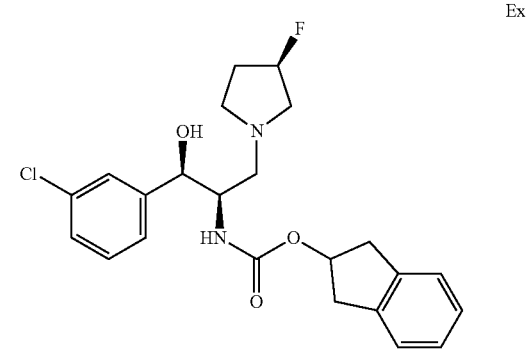
Ex. 16
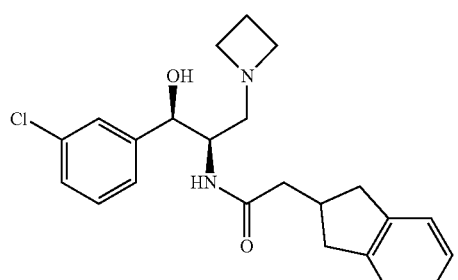
Ex. 17
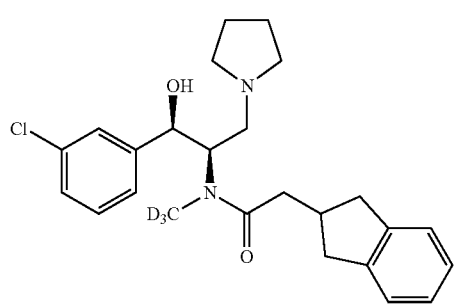
Ex. 18
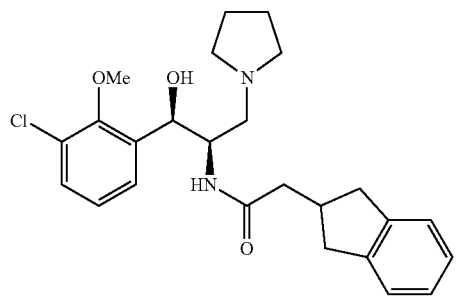
Ex. 19
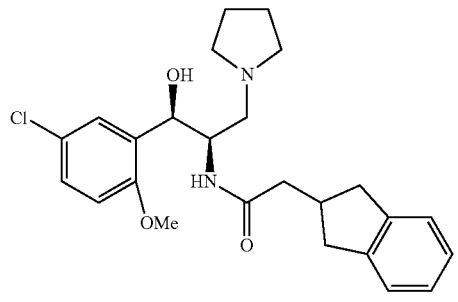
Ex. 20
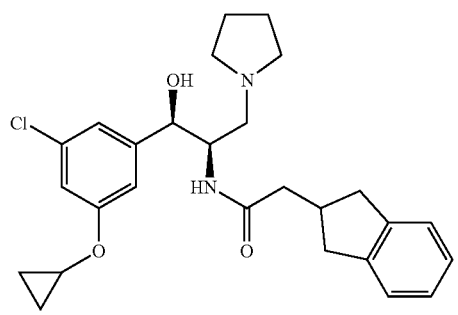

Ex. 21

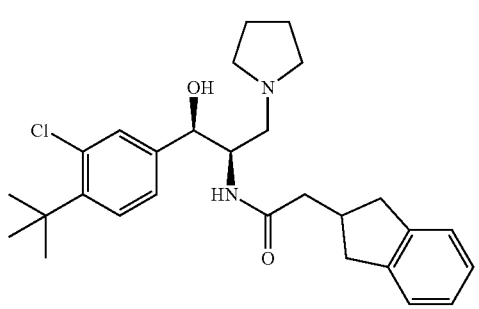

Ex. 22

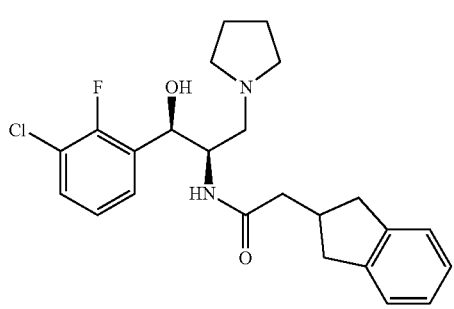

Ex. 23

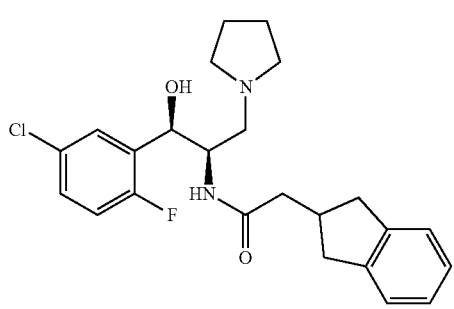

Synthesis of Compounds

Compounds of the present invention were prepared as follows. The following synthetic schemes are representative of the reactions used to synthesize compounds of structural formula (I). Modifications and alternate schemes to prepare GCS inhibitors of the invention are readily within the capabilities of persons skilled in the art.

Preparation and Spectroscopic Data of Compounds of Structural Formula (I)

Chemical names follow CAS or IUPAC nomenclature. Starting materials were purchased from Fisher, Sigma-Aldrich Lancaster, Fluka, or TCI-America, and were used without purification. All reaction solvents were purchased from Fisher and used as received. Reactions were monitored by TLC using pre-coated silica gel 60 F254 plates. Silica gel chromatography was performed with silica gel (220-240 mesh) obtained from Silicycle.

NMR spectra were recorded on a Bruker 500 MHz spectrometer. Chemical shifts are reported in δ (parts per million) by reference to the hydrogenated residues of deuterated solvent as internal standard $CDCL_3$: δ=7.28 ($^1$H NMR). Mass spectra were recorded on a Micromass LCT time-of-flight instrument utilizing the positive electrospray ionization mode. The purity of the compounds was assessed via analytical reverse phase HPLC with a gradient of 10-90% $CH_3CN$/water over 6 minutes (Agilent Eclipse Plus C18 4.6×75 mm column (3.5 μm silica), 254 nm detection).

Unless otherwise stated all temperatures are in degrees Celsius.

In these examples and elsewhere, abbreviations have the following meanings:
NMR=proton nuclear magnetic resonance
$Boc_2O$=di-tert-butyl dicarbonate
$CH_3CN$=acetonitrile
aq.=aqueous
d=doublet
Cbz=benzyl chloroformate
$CH_2Cl_2$=dichloromethane
$CH_3I$=methyl iodide
CuI=cuprous iodide
$Cs_2CO_3$=cesium carbonate
DMAP=4-dimethylaminopyridine
DIPEA=N,N-diisopropylethylamine
DMF=dimethylformamide
EDTA=ethylenediaminetetraacetic acid
ESI=electrospray ionization
EtOAc=ethyl acetate
FBS=fetal bovine serum
g=gram
GlcCer=glucosyl ceramide
h=hours
HCl=hydrochloric acid
HF=hydrofluoric acid
$HCO_2H$=formic acid
$H_2O$=water
HATU=1-[bis(dimethylamino)methylene]-1H-1,2,3-triazolo[4,5-b]pyridinium 3-oxid hexafluorophosphate
HEPES=4-(2-hydroxyethyl)-1-piperazineethanesulfonic acid
HPLC=high performance liquid chromatography
iPrMgCl=isopropyl magnesium chloride
kg=kilogram
$K_2CO_3$=potassium carbonate
KI=potassium iodide
$K_3PO_4$=potassium phosphate
LiCl=lithium chloride
m=multiplet
mg=milligrams
Me=methyl
MeOH=methanol
$MgSO_4$=magnesium sulfate
MHz=megahertz
min=minutes
mL=milliliters
mM=millimolar
mmol=millimole
MOMCl=methoxymethyl chloride
ESI-MS=mass spectrometry (electrospray ionization)
N=normal
nm=nanomolar
$N_2$=nitrogen gas
$NaH_4Cl$=ammonium chloride
NaH=sodium hydride
NaI=Sodium iodide
$NaHCO_3$=sodium bicarbonate
NaCl=sodium chloride
NaOH=sodium hydroxide
$NaNo_2$=sodium nitrite
$Na_2SO_4$=sodium sulfate
$Pd(OAc)_2$=palladium(II)acetate
PBS=phosphate buffered saline
Ph=phenyl
psi=pounds per square inch
$t_R$=retention time rt or RT=room temperature
s=singlet
satd.=saturated
t=triplet
THF=tetrahydrofuran
TosCl=tosyl chloride
TBDMSCl=tert-butyldimethylsilyl chloride
TFA=trifluoroacetic acid
µg=microgram
µL=microliter
µmol=micromolar
U/mL=units per milliliter
UV=ultraviolet
v=volume
δ=chemical shift

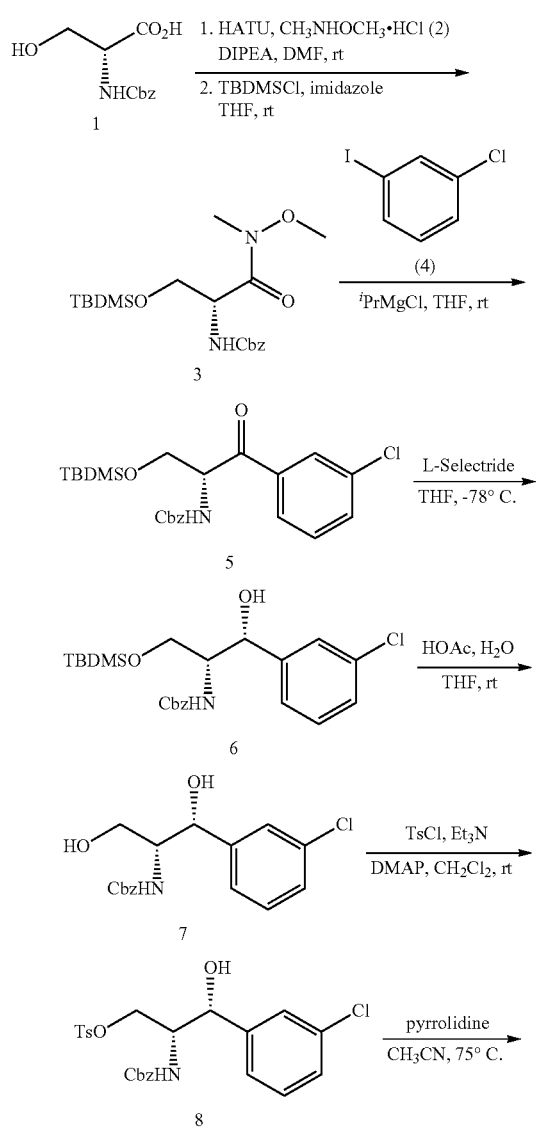

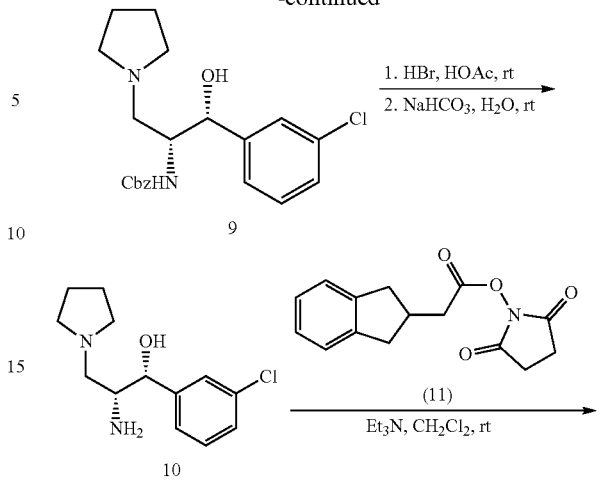

Example 1

Preparation of (R)-benzyl (3,8,8,9,9-pentamethyl-4-oxo-2,7-dioxa-3-aza-8-siladecan-5-yl)carbamate (3)

To a mixture of compound 1 (5.00 g, 24.4 mmol), compound 2 (7.15 g, 73.5 mmol), and DIPEA (15.8 g, 122 mmol) in anhydrous CH$_3$CN (60 mL) was added HATU (9.70 g, 25.5 mmol) at rt under N$_2$. The resulting mixture was stirred for overnight. The reaction mixture was then petitioned between water and EtOAc. The organic layer was dried over anhydrous Na$_2$SO$_4$, filtered, and concentrated under reduced pressure. The residue was dried under high vacuum and then dissolved in THF (60 mL). To the resulting solution was added imidazole (2.99 g, 43.9 mmol) followed by TBDMSCl (5.50 g, 36.5 mmol). The reaction mixture was stirred overnight at rt. The reaction mixture was then concentrated under reduced pressure. The residue was petitioned between water and EtOAc. The organic layer was dried over anhydrous Na$_2$SO$_4$, filtered, and concentrated under reduced pressure. The resulting residue was purified by flash column chromatography on silica gel eluting with 10% to 30% EtOAc/hexanes to afford compound 3 as a clear oil (7.10 g, 73%): $^1$H NMR (500 MHz, CDCl$_3$) δ 7.33-7.28 (m, 5H), 5.60 (d, J=8.5 Hz, 1H), 5.08 (ABq, J=12.3 Hz, 2H), 4.78 (br s, 1H), 3.88-3.78 (m, 2H), 3.74 (s, 3H), 3.20 (s, 3H), 0.84 (s, 9H), 0.01 (s, 6H).

Preparation of (R)-benzyl (3-((tert-butyldimethylsilyl)oxy)-1-(3-chlorophenyl)-1-oxopropan-2-yl)carbamate (5)

To a stirred mixture of compound 4 (5.59 g, 23.4 mmol) in anhydrous THF (100 mL) was added 2M $^i$PrMgCl solution in THF (25.5 mL, 51.0 mmol) dropwise at rt under $N_2$. The resulting mixture was stirred for 30 min. To the resulting mixture was added a solution of compound 3 (7.20 g, 18.2 mmol) in anhydrous THF (30 mL). The reaction mixture was stirred at rt for 1 h and then cooled to −20° C., quenched with saturated $NH_4Cl$ aqueous solution, extracted with EtOAc. The combined extracts were dried over anhydrous $Na_2SO_4$, filtered, and concentrated under reduced pressure. The resulting residue was purified by flash column chromatography on silica gel eluting with 4% to 16% EtOAc/hexanes to afford compound 5 as a clear oil (7.58 g, 93%): ESI MS, m/z=448 $[M+H]^+$.

Preparation of benzyl ((1R,2R)-3-((tert-butyldimethylsilyl)oxy)-1-(3-chlorophenyl)-1-hydroxypropan-2-yl)carbamate (6)

To a stirred solution of compound 5 (7.58 g, 16.9 mmol) in anhydrous THF (80 mL) was added 1M L-Selectride solution in THF (33.8 mL, 33.8 mmol) dropwise at −78° C. under $N_2$. The resulting mixture was stirred at −78° C. for 1 h and then quenched with saturated $NH_4Cl$ aqueous solution, extracted with EtOAc. The combined extracts were dried over anhydrous $Na_2SO_4$, filtered, and concentrated under reduced pressure. The resulting residue was purified by flash column chromatography on silica gel eluting with 8% to 30% EtOAc/hexanes to afford compound 6 as a clear oil (7.11 g, 93%): ESI MS, m/z=450 $[M+H]^+$.

Preparation of benzyl ((1R,2R)-1-(3-chlorophenyl)-1,3-dihydroxypropan-2-yl)carbamate (7)

A solution of compound 6 (7.11 g, 15.8 mmol) in HOAc (40 mL), THF (20 mL), and water (20 mL) was stirred at rt for overnight and then concentrated under reduced pressure. The residue was dissolved in EtOAc and washed with water. The organic layer was dried over anhydrous $Na_2SO_4$, filtered, and concentrated under reduced pressure. The resulting residue was purified by flash column chromatography on silica gel eluting with 20% to 100% EtOAc/hexanes to afford compound 7 as a clear syrup (4.92 g, 93%): ESI MS, m/z=336 $[M+H]^+$.

Preparation of (2R,3R)-2-(((benzyloxy)carbonyl)amino)-3-(3-chlorophenyl)-3-hydroxypropyl 4-methylbenzenesulfonate (8)

To a stirred solution of compound 7 (4.92 g, 14.7 mmol), $Et_3N$ (4.43 g, 43.8 mmol), and DMAP (179 mg, 1.47 mmol) in anhydrous $CH_2Cl_2$ (40 mL) was added a solution of TsCl (3.07 g, 16.1 mmol) in anhydrous $CH_2Cl_2$ (120 mL) dropwise over 2 h (syringe pump used) at rt under $N_2$. The reaction mixture was stirred for 1 h and then concentrated under reduced pressure (water bath temperature below 30° C.). The resulting residue was directly purified by flash column chromatography on silica gel eluting with 10% to 40% EtOAc/hexanes to afford compound 8 as a white foam (6.69 g, 93%): ESI MS, m/z=490 $[M+H]^+$.

Preparation of benzyl ((1R,2R)-1-(3-chlorophenyl)-1-hydroxy-3-(pyrrolidin-1-yl)propan-2-yl)carbamate (9)

A solution of compound 8 (6.69 g, 13.7 mmol) and pyrrolidine (4.86 g, 68.3 mmol) in anhydrous $CH_3CN$ (80 mL) was heated at 75° C. oil bath for 2 h, then cooled to rt, and concentrated under reduced pressure. The resulting residue was purified by flash column chromatography on silica gel eluting with 2% to 20% $MeOH/CH_2Cl_2$ to afford compound 9 as a light yellow foam (2.85 g, 54%): ESI MS, m/z=389 $[M+H]^+$.

Preparation of (1R,2R)-2-amino-1-(3-chlorophenyl)-3-(pyrrolidin-1-yl)propan-1-ol (10)

To a stirred solution of compound 9 (2.85 g, 7.33 mmol) in HOAc (75 mL) was added a 33% aq HBr solution in HOAc (15 mL) at rt. The reaction mixture was stirred at rt for 4 h, then concentrated under reduced pressure. The resulting residue was basified by 6N NaOH aqueous solution to pH 9 with an ice/water cooling bath and then extracted with $^iPrOH/CHCl_3$ (1:10) (LC/MS monitoring the aqueous phase). The combined extracts were dried over anhydrous $Na_2SO_4$, filtered, and concentrated under reduced pressure. The resulting residue was purified by C18 column eluting with 0% to 100% $CH_3CN/H_2O$ (with 0.05% TFA). The fractions contained desired product were combined, concentrated under reduced pressure. The residue was basified by saturated aqueous $NaHCO_3$ and extracted with $^iPrOH/CHCl_3$ (1:10) (LC/MS monitoring the aqueous phase). The combined extracts were dried over anhydrous $Na_2SO_4$, filtered, and concentrated under reduced pressure to afford compound 10 as a clear oil (910 mg, 49%): ESI MS, m/z=255 $[M+H]^+$.

Preparation of 2,5-dioxopyrrolidin-1-yl 2-(2,3-dihydro-1H-inden-2-yl)acetate (11)

To a solution of N-hydroxysuccinimide (1.94 g, 17.0 mmol) in $CH_2Cl_2$ (100 mL) was added 2-(2,3-dihydro-1H-inden-2-yl)acetic acid (3.00 g, 17.0 mmol) and EDC (3.58 g, 18.0 mmol). The resulting solution was stirred at rt for 18 h. The reaction mixture was diluted with saturated sodium bicarbonate (100 mL). The layers were separated and the aqueous was extracted with $CH_2Cl_2$. The combined organic extracts were washed with saturated brine, dried over anhydrous $Na_2SO_4$, filtered, and concentrated under reduced pressure to give compound 11 (4.40 g, 94%) as an off-white solid: ESI MS m/z 296 $[M+Na]^+$.

Preparation of N-((1R,2R)-1-(3-chlorophenyl)-1-hydroxy-3-(pyrrolidin-1-yl)propan-2-yl)-2-(2,3-dihydro-1H-inden-2-yl)acetamide (Example 1)

A solution of compound 10 (910 mg, 3.57 mmol), compound 11 (1.07 g, 3.92 mmol) and $Et_3N$ (1.09 g, 10.8 mmol) in anhydrous $CH_2Cl_2$ (50 mL) was stirred at rt for overnight. The reaction mixture was diluted with $CH_2Cl_2$, washed with saturated aqueous $NaHCO_3$, dried over anhydrous $Na_2SO_4$, filtered, and concentrated under reduced pressure. The resulting residue was purified by flash column chromatography on silica gel eluting with 4% to 30% $MeOH/CH_2Cl_2$ and further purified by C18 column eluting with 0% to 100% $CH_3CN/H_2O$ (with 0.05% TFA). The fractions contained desired product were combined, concentrated under reduced pressure. The residue was basified by saturated aqueous $NaHCO_3$ and extracted with $CH_2Cl_2$. The combined extracts were dried over anhydrous $Na_2SO_4$, filtered, and concentrated under reduced pressure to afford compound Example 1 as a white solid (884 mg, 60%): $^1H$ NMR (500 MHz, $CDCl_3$) δ 7.40-7.25 (m, 3H), 7.21-7.11 (m, 5H), 5.88 (d, J=7.5 Hz, 1H), 5.07 (d, J=2.7 Hz, 1H), 4.26-4.23 (m, 1H), 3.00-2.63 (m, 9H), 2.49 (dd, J=15.6, 6.7 Hz, 1H), 2.33 (dd, J=15.6, 6.6 Hz, 1H), 2.28 (dd, J=14.1, 7.1 Hz, 1H), 2.18 (dd, J=14.1, 8.1 Hz, 1H), 1.85-1.75 (m, 4H); ESI MS, m/z=413 $[M+H]^+$.

The following compounds were prepared as in Representative Scheme 1 using with the requisite commercially available aryl iodide in place of compound 4.

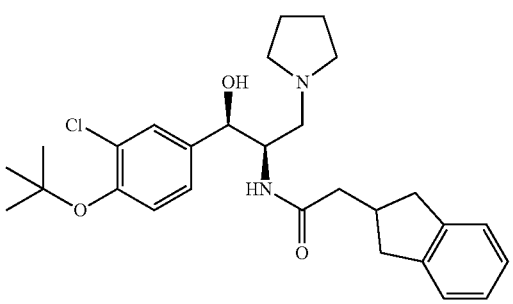 [SMILES: CC(C)(C)Oc1ccc([C@@H](O)[C@@H](CN2CCCC2)NC(=O)CC2Cc3ccccc3C2)cc1Cl]

N-((1R,2R)-1-(4-(tert-butoxy)-3-chlorophenyl)-1-hydroxy-3-(pyrrolidin-1-yl)propan-2-yl)-2-(2,3-dihydro-1H-inden-2-yl)acetamide (Example 2)

¹H NMR (300 MHz, DMSO-d₆) δ 7.55-7.52 (m, 1H), 7.40 (d, J=1.8 Hz, 1H), 7.19-7.06 (m, 6H), 5.80 (bs, 1H), 4.81 (s, 1H), 4.26-4.05 (m, 1H), 2.90-2.65 (m, 3H), 2.60-2.40 (m, 5H), 2.39-2.05 (m, 4H), 1.68 (bs, 4H), 1.32 (s, 9H); ESI MS, m/z=485 [M+H]⁺.

N-((1R,2R)-1-(3-chloro-4-(trifluoromethoxy)phenyl)-1-hydroxy-3-(pyrrolidin-1-yl)propan-2-yl)-2-(2,3-dihydro-1H-inden-2-yl)acetamide (Example 3)

¹H NMR (500 MHz, CDCl₃) δ 7.53 (d, J=1.9 Hz, 1H), 7.32-7.28 (m, 1H), 7.27-7.23 (m, 1H), 7.15-7.08 (m, 4H), 5.99-5.90 (m, 1H), 5.11-5.07 (m, 1H), 4.30-4.24 (m, 1H), 3.04-2.96 (m, 2H), 2.95-2.83 (m, 2H), 2.82-2.62 (m, 5H), 2.54-2.44 (m, 1H), 2.37-2.24 (m, 2H), 2.22-2.13 (m, 1H), 1.91-1.77 (m, 4H); ESI MS m/z 497 [M+H]⁺.

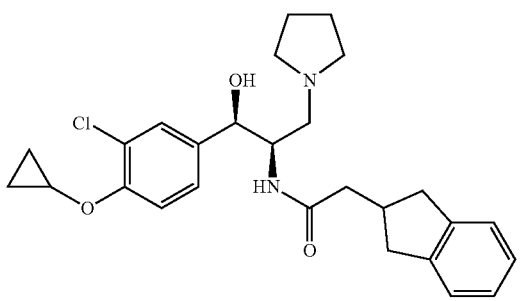 [SMILES: O=C(CC1Cc2ccccc2C1)N[C@H](CN1CCCC1)[C@H](O)c1ccc(OC2CC2)c(Cl)c1]

N-((1R,2R)-1-(3-chloro-4-cyclopropoxyphenyl)-1-hydroxy-3-(pyrrolidin-1-yl)propan-2-yl)-2-(2,3-dihydro-1H-inden-2-yl)acetamide (Example 4)

¹H NMR (500 MHz, CDCl₃) δ 7.38-7.37 (m, 1H), 7.25-7.11 (m, 6H), 5.89 (d, J=7.6 Hz, 1H), 5.01 (d, J=2.8 Hz, 1H), 4.26-4.20 (m, 1H), 3.80-3.75 (m, 1H), 2.99 (dd, J=15.6, 7.7 Hz, 1H), 2.94-2.83 (m, 3H), 2.81-2.62 (m, 5H), 2.51 (dd, J=15.6, 6.7 Hz, 1H), 2.37 (dd, J=15.6, 6.6 Hz, 1H), 2.30 (dd, J=14.0, 7.0 Hz, 1H), 2.20 (dd, J=14.1, 8.1 Hz, 1H), 1.85-1.75 (m, 4H), 0.85-0.75 (m, 4H); ESI MS, m/z=469 [M+H]⁺.

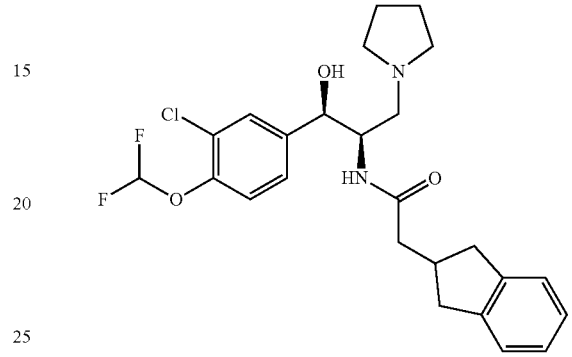

N-((1R,2R)-1-(3-chloro-4-(difluoromethoxy)phenyl)-1-hydroxy-3-(pyrrolidin-1-yl)propan-2-yl)-2-(2,3-dihydro-1H-inden-2-yl)acetamide (Example 13)

¹H NMR (500 MHz, CDCl₃) δ 7.50-7.49 (m, 1H), 7.24-7.20 (m, 2H), 7.16-7.10 (m, 4H), 6.49 (t, J=73.5 Hz, 1H), 5.92 (d, J=7.6 Hz, 1H), 5.06 (d, J=2.6 Hz, 1H), 4.26-4.22 (m, 1H), 3.02-2.95 (m, 2H), 2.91-2.85 (m, 2H), 2.78-2.62 (m, 5H), 2.50 (dd, J=15.6, 6.7 Hz, 1H), 2.35 (dd, J=15.6, 6.6 Hz, 1H), 2.29 (dd, J=14.2, 7.1 Hz, 1H), 2.19 (dd, J=14.2, 8.0 Hz, 1H), 1.85-1.76 (m, 4H); ESI MS, m/z=479 [M+H]⁺.

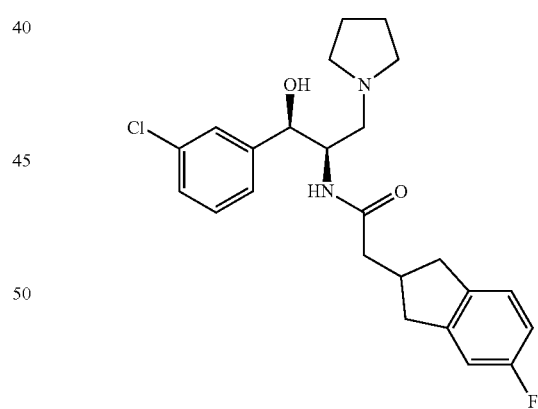

N-((1R,2R)-1-(3-chlorophenyl)-1-hydroxy-3-(pyrrolidin-1-yl)propan-2-yl)-2-(5-fluoro-2,3-dihydro-1H-inden-2-yl)acetamide (Example 9)

Prepared as in Representative Scheme 1 using 2-(5-fluoro-2,3-dihydro-1H-inden-2-yl)acetic acid in place of 2-(2,3-dihydro-1H-inden-2-yl)acetic acid. ¹H NMR (500 MHz, DMSO-d₆) δ 7.52 (bs, 1H), 7.39 (s, 1H), 7.35-7.23 (m, 3H), 7.12 (m, 1H), 6.96-6.86 (m, 2H), 5.72 (bs, 1H), 4.86 (s, 1H), 4.12 (bs, 1H), 2.76-2.68 (m, 2H), 2.67-2.23 (m, 8H), 2.18-2.05 (m, 2H), 1.68 (bs, 4H); ESI MS, m/z=431 [M+H]⁺.

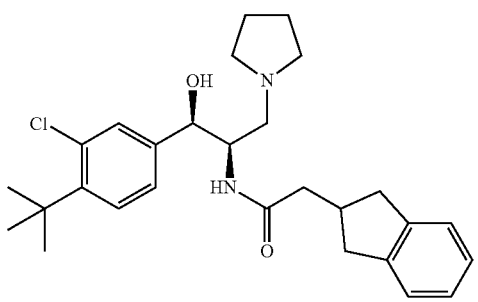 [SMILES: CC(C)(C)c1ccc([C@@H](O)[C@@H](CN2CCCC2)NC(=O)CC2Cc3ccccc3C2)cc1Cl]

N-((1R,2R)-1-(4-(tert-butyl)-3-chlorophenyl)-1-hydroxy-3-(pyrrolidin-1-yl)propan-2-yl)-2-(2,3-dihydro-1H-inden-2-yl)acetamide (Example 21)

ESI MS, m/z=469.2 [M+H]+.

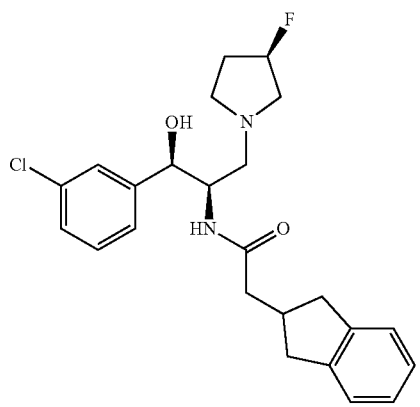 [SMILES: O=C(CC1Cc2ccccc2C1)N[C@H](CN1CC[C@@H](F)C1)[C@H](O)c1cccc(Cl)c1]

N-((1R,2R)-1-(3-chlorophenyl)-3-((R)-3-fluoropyrrolidin-1-yl)-1-hyroxypropan-2-yl)-2-(2,3-dihydro-1H-inden-2-yl)acetamide (Example 10)

Prepared as in Representative Scheme 1 using (R)-3-fluoropyrrolidine instead of pyrrolidine. $^1$H NMR (300 MHz, CDCl$_3$) δ 7.40 (s, 1H), 7.32-7.24 (m, 2H), 7.23-7.10 (m, 5H), 5.99 (d, J=7.2 Hz, 1H), 5.28-5.05 (m, 2H), 4.25-4.18 (m, 1H), 3.18-2.67 (m, 8H), 2.65-2.46 (m, 2H), 2.38-1.96 (m, 5H); ESI MS, m/z=431 [M+H]+.

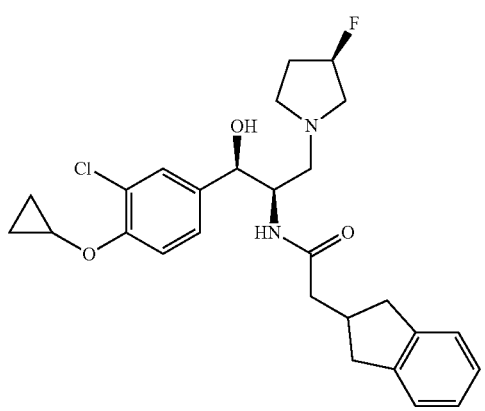 [SMILES: O=C(CC1Cc2ccccc2C1)N[C@H](CN1CC[C@@H](F)C1)[C@H](O)c1ccc(OC2CC2)c(Cl)c1]

N-((1R,2R)-1-(3-chloro-4-cyclopropoxyphenyl)-3-((R)-3-fluoropyrrolidin-1-yl)-1-hydroxypropan-2-yl)-2-(2,3-dihydro-1H-inden-2-yl)acetamide (Example 11)

Prepared as described for Example 4 using (R)-3-fluoropyrrolidine instead of pyrrolidine. $^1$H NMR (500 MHz, CDCl$_3$) δ 7.38 (d, J=2.1 Hz, 1H), 7.38-7.25 (m, 1H), 7.19-7.10 (m, 5H), 5.98 (d, J=6.6 Hz, 1H), 5.23-5.10 (m, 1H), 4.99 (d, J=3.1 Hz, 1H), 4.23-4.17 (m, 1H), 3.79-3.75 (m, 1H), 3.14-2.98 (m, 3H), 2.92-2.49 (m, 7H), 2.39 (dd, J=15.6, 6.7 Hz, 1H), 2.32 (dd, J=14.1, 7.1 Hz, 1H), 2.23 (dd, J=14.1, 8.0 Hz, 1H), 2.19-2.04 (m, 2H), 0.83-0.79 (m, 4H); ESI MS, m/z=487 [M+H]+.

N-((1R,2R)-3-(azetidin-1-yl)-1-(3-chlorophenyl)-1-hydroxypropan-2-yl)-2-(2,3-dihydro-1H-inden-2-yl) acetamide (Example 16)

Prepared as in Scheme 1 using azetidine instead of pyrrolidine. $^1$H NMR (499 MHz, Chloroform-d) δ 7.40 (s, 1H), 7.32-7.23 (m, 2H), 7.23-7.16 (m, 1H), 7.13 (br s, 4H), 5.81 (d, J=7.8 Hz, 1H), 5.04 (d, J=2.1 Hz, 1H), 4.12 (dq, J=6.6, 3.2 Hz, 1H), 3.36 (dq, J=23.1, 7.1 Hz, 4H), 3.02 (dd, J=12.8, 3.9 Hz, 1H), 2.95 (dd, J=15.6, 7.7 Hz, 1H), 2.85 (dd, J=12.8, 3.2 Hz, 1H), 2.79 (dd, J=15.4, 7.7 Hz, 1H) 2.71 (hept, J=7.1 Hz, 1H), 2.47 (dd, J=15.6, 6.8 Hz, 1H), 2.30-2.20 (m, 2H), 2.19-2.06 (m, 3H); HRMS (ESI) m/z: Calcd for [M+H]+ 399.1839; Found: 399.1832.

The following compounds were prepared as in Representative Scheme 1 using non-commercial aryl iodides in place of compound 4. The syntheses of these iodides is included below.

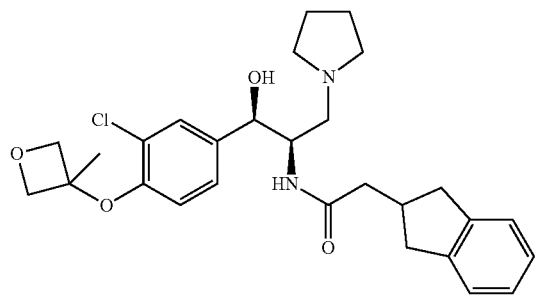 [SMILES: CC1(Oc2ccc([C@@H](O)[C@@H](CN3CCCC3)NC(=O)CC3Cc4ccccc4C3)cc2Cl)COC1]

N-((1R,2R)-1-(3-chloro-4-((3-methyloxetan-3-yl)oxy)phenyl)-1-hydroxy-3-(pyrrolidin-1-yl)propan-2-yl)-2-(2,3-dihydro-1H-inden-2-yl)acetamide (Example 5)

Prepared as in Scheme 1 using 3-(2-chloro-4-iodophenoxy)-3-methyloxetane. $^1$H NMR (500 MHz, CDCl$_3$) δ 7.44-7.43 (m, 1H), 7.17-7.08 (m, 5H), 6.43 (d, J=8.5 Hz, 1H), 5.91 (d, J=7.5 Hz, 1H), 5.00 (d, J=2.8 Hz, 1H), 4.96 (d, J=6.6 Hz, 2H), 4.55 (d, J=7.2 Hz, 2H), 4.26-4.20 (m, 1H), 3.01 (dd, J=15.6, 7.7 Hz, 1H), 2.94-2.83 (m, 3H), 2.81-2.61 (m, 5H), 2.52 (dd, J=15.6, 6.6 Hz, 1H), 2.38 (dd, J=15.6, 6.6 Hz, 1H), 2.30 (dd, J=14.1, 7.1 Hz, 1H), 2.20 (dd, J=14.1, 8.1 Hz, 1H), 1.85-1.75 (m, 4H), 1.73 (s, 3H); ESI MS, m/z=499 [M+H]+.

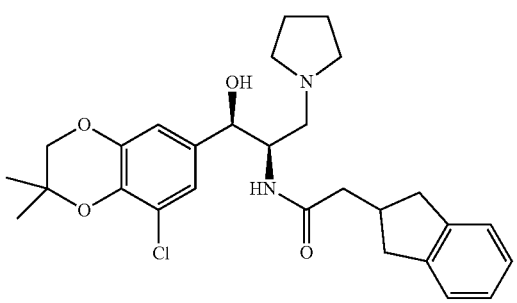 [SMILES: CC1(C)COc2cc([C@@H](O)[C@@H](CN3CCCC3)NC(=O)CC3Cc4ccccc4C3)cc(Cl)c2O1]

N-((1R,2R)-1-(8-chloro-2,2-dimethyl-2,3-dihydrobenzo[b][1,4]dioxin-6-yl)-1-hydroxy-3-(pyrrolidin-1-yl)propan-2-yl)-2-(2,3-dihydro-1H-inden-2-yl)acetamide (Example 7)

Prepared as in Scheme 1 using 8-chloro-6-iodo-2,2-dimethyl-2,3-dihydrobenzo[b][1,4]dioxine. $^{1}$H NMR (500 MHz, CDCl$_3$) δ 7.17-7.11 (m, 4H), 6.97-6.96 (m, 1H), 6.80-6.79 (m, 1H), 5.88 (d, J=7.4 Hz, 1H), 4.94 (d, J=2.9 Hz, 1H), 4.20-4.17 (m, 1H), 3.84 (ABq, J=11.1 Hz, 2H), 3.01 (dd, J=15.6, 7.9 Hz, 1H), 2.94-2.85 (m, 3H), 2.80-2.61 (m, 5H), 2.52 (dd, J=15.6, 6.7 Hz, 1H), 2.41 (dd, J=15.6, 6.7 Hz, 1H), 2.30 (dd, J=14.1, 7.1 Hz, 1H), 2.22 (dd, J=14.0, 8.1 Hz, 1H), 1.83-1.75 (m, 4H), 1.37 (s, 6H); ESI MS, m/z=499 [M+H]$^{+}$.

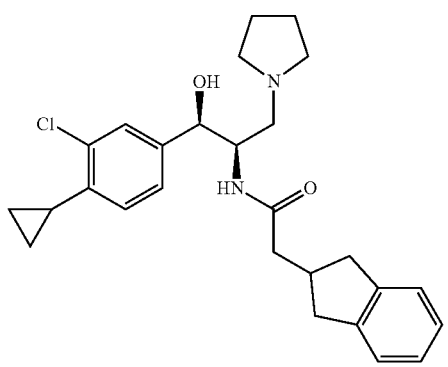 [SMILES: O=C(CC1Cc2ccccc2C1)N[C@H](CN1CCCC1)[C@H](O)c1ccc(C2CC2)c(Cl)c1]

N-((1R,2R)-1-(3-chloro-4-cyclopropylphenyl)-1-hydroxy-3-(pyrrolidin-1-yl)propan-2-yl)-2-(2,3-dihydro-1H-inden-2-yl)acetamide (Example 8)

Prepared as in Scheme 1 using 3-chloro-4-cyclopropyl-1-iodobenzene. $^{1}$H NMR (500 MHz, DMSO-d$_6$) δ 7.52-7.48 (m, 1H), 7.36 (s, 1H), 7.18-7.05 (m, 5H), 6.93 (d, J=8.5 Hz, 1H), 5.65 (bs, 1H), 4.81 (s, 1H), 4.10 (bs, 1H), 2.78-2.72 (m, 2H), 2.67-2.45 (m, 4H), 2.41 (dd, J=15.5, 7.5 Hz, 1H), 2.30-2.25 (m, 3H), 2.18-2.11 (m, 3H), 1.68 (bs, 4H), 0.98 (m, 2H), 0.65 (m, 2H); ESI MS, m/z=453 [M+H]$^{+}$.

Preparation of tert-butyl (4-bromo-3-chlorophenyl)carbamate

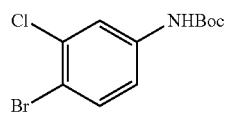

To a stirred solution of compound 4-bromo-3-chloroaniline (19.5 g, 94.4 mmol) in water (200 mL) was added Boc$_2$O (30.9 g, 142 mmol) at rt. The resulting mixture was stirred for overnight at rt. The reaction mixture was then extracted with EtOAc (3×). The organic layer was dried over anhydrous Na$_2$SO$_4$, filtered, and concentrated under reduced pressure. The resulting residue was purified by flash column chromatography on silica gel eluting with 5% to 20% EtOAc/hexanes to afford compound 2 as a purple solid (21.5 g, 63%): $^{1}$H NMR (300 MHz, DMSO-d$_6$) δ 9.71 (br s, 1H), 7.78 (d, J=2.3 Hz, 1H), 7.62 (d, J=8.8 Hz, 1H), 7.31 (dd, J=8.8, 2.4 Hz, 1H), 1.47 (s, 9H).

Preparation of tert-butyl (3-chloro-4-cyclopropylphenyl)carbamate

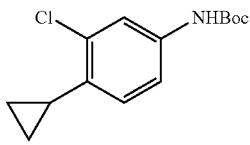 [SMILES: CC(C)(C)OC(=O)Nc1ccc(C2CC2)c(Cl)c1]

A mixture of tert-butyl (4-bromo-3-chlorophenyl)carbamate (620 mg, 2.02 mmol), cyclopropyltrifluoro-λ$^{4}$-borane, potassium salt (578 mg, 4.04 mmol), P(Cy)$_3$ (113 mg, 0.403 mmol), and K$_3$P4 (1.50 g, 7.07 mmol) in water (5 mL) and toluene (10 mL) in a seal tube was bubbled with argon for 5 min. To the resulting mixture was added Pd(OAc)$_2$ (45 mg, 0.200 mmol) at rt. The resulting mixture was sealed and heated at 110° C. for overnight. After this time, the reaction mixture was cooled to rt and extracted with EtOAc (3×). The organic layer was dried over anhydrous Na$_2$SO$_4$, filtered, and concentrated under reduced pressure. The resulting residue was purified by flash column chromatography on silica gel eluting with 0.5% to 2% EtOAc/hexanes to afford title compound as a yellow oil (370 mg, 68%): $^{1}$H NMR (500 MHz, DMSO-d$_6$) δ 9.42 (br s, 1H), 7.58 (d, J=1.3 Hz, 1H), 7.24 (dd, J=8.5, 2.1 Hz, 1H), 6.91 (d, J=8.5 Hz, 1H), 1.98-2.08 (m, 1H), 1.47 (s, 9H), 0.94-0.91 (m, 2H), 0.62-0.60 (m, 2H).

Preparation of 3-chloro-4-cyclopropylaniline

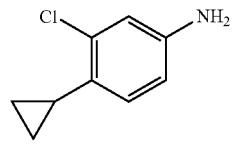 [SMILES: Nc1ccc(C2CC2)c(Cl)c1]

To a stirred solution of tert-butyl (3-chloro-4-cyclopropylphenyl)carbamate (2.25 g, 8.40 mmol) in 1,2-dichloroethane (60 mL) was added Montmorillnite K10 (450 mg) at rt. The resulting mixture was heated at 88° C. for 2 h. After this time, the reaction mixture was cooled to rt, diluted with CH$_2$Cl$_2$, and filtered. The filtrate was concentrated under reduced pressure. The resulting residue was purified by flash column chromatography on silica gel eluting with 5% to 20% EtOAc/hexanes to afford title compound as a clear oil (1.40 g, quant.): $^{1}$H NMR (500 MHz, DMSO-d$_6$) δ 6.69 (d, J=8.3 Hz, 1H), 6.59 (d, J=2.3 Hz, 1H), 6.41 (dd, J=8.3, 2.3 Hz, 1H), 5.14 (s, 2H), 1.86-1.99 (m, 1H), 0.80-0.84 (m, 2H), 0.45-0.52 (m, 2H).

Preparation of 2-chloro-1-cyclopropyl-4-iodobenzene

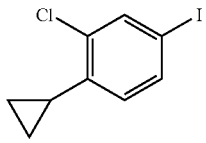 [SMILES: Clc1cc(I)ccc1C1CC1]

To a stirred solution of 3-chloro-4-cyclopropylaniline (1.26 g, 7.52 mmol) in 5N aqueous HCl (24 mL) was added a solution of NaNO$_2$ (778 mg, 11.3 mmol) in water (10 mL) at 0° C. dropwise. The resulting mixture was then stirred at 0° C. for 1 h. After this time, to the reaction mixture was added a solution of KI (2.74 g, 16.5 mmol) in water (5 mL) dropwise. The reaction mixture was stirred 30 min at 0° C. and warmed to rt. After stirred at rt for 2 h, the reaction mixture was basified with 6N NaOH aq. and extracted with EtOAc (3×). The combined extracts were washed with brine, dried over anhydrous Na$_2$SO$_4$, filtered, and concentrated under reduced pressure. The resulting residue was dried under high vacuum to afford title compound as a brown solid (1.76 g, 84%): $^1$H NMR (500 MHz, DMSO-d$_6$) δ 7.76 (d, J=1.7 Hz, 1H), 7.57 (dd, J=8.2, 1.6 Hz, 1H), 6.81 (d, J=8.2 Hz, 1H), 2.06-2.11 (m, 1H), 0.98-1.02 (m, 2H), 0.68-0.70 (m, 2H).

Preparation of diethyl 2-(4-bromo-2-chlorophenoxy)malonate

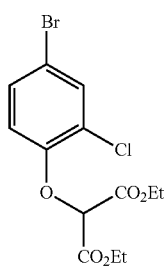 [SMILES: CCOC(=O)C(Oc1ccc(Br)cc1Cl)C(=O)OCC]

A mixture of 4-bromo-2-chlorophenol (15.0 g, 72.3 mmol), ClCH(CO$_2$Et)$_2$ (14.1 g, 72.4 mmol), and K$_2$CO$_3$ (25.0 g, 181 mmol) in anhydrous CH$_3$CN (150 mL) was stirred at rt over weekend. The reaction mixture was then filtered. The filtrate was concentrated under reduced pressure. The resulting residue was purified by flash column chromatography on silica gel eluting with 5% to 10% EtOAc/hexanes to afford title compound as a clear oil (20.5 g, 78%): $^1$H NMR (300 MHz, CDCl$_3$) δ 7.55 (d, J=2.3 Hz, 1H), 7.31 (dd, J=8.7, 2.4 Hz, 1H), 6.85 (d, J=8.7 Hz, 1H), 5.14 (s, 1H), 4.40-4.27 (m, 4H), 1.33-1.23 (m, 6H).

Preparation of diethyl 2-(4-bromo-2-chlorophenoxy)-2-methylmalonate

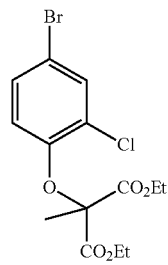

A mixture of diethyl 2-(4-bromo-2-chlorophenoxy)malonate (20.5 g, 56.1 mmol) and Cs$_2$CO$_3$ (27.4 g, 84.1 mmol) in anhydrous DMF (120 mL) was stirred at rt for 30 min. To the resulting mixture was added CH$_3$I (11.9 g, 83.8 mmol) and stirred for overnight. After this time, the reaction mixture was diluted with ice cold water (200 mL), extracted with 1:1 EtOAc/hexanes (3×250 mL). The combined extracts were washed with 10% LiCl aqueous solution (2×100 mL) and brine (100 mL), dried over anhydrous Na$_2$SO$_4$, filtered, and concentrated under reduced pressure. The resulting residue was purified by flash column chromatography on silica gel eluting with 5% to 10% EtOAc/hexanes to afford title compound as a clear oil (18.9 g, 89%): $^1$H NMR (500 MHz, CDCl$_3$) δ 7.52 (d, J=2.4 Hz, 1H), 7.27-7.25 (m, 1H), 7.01 (d, J=8.8 Hz, 1H), 4.28 (q, J=7.2 Hz, 4H), 1.72 (s, 3H), 1.27 (t, J=7.2 Hz, 6H).

Preparation of 2-(4-bromo-2-chlorophenoxy)-2-methylpropane-1,3-diol

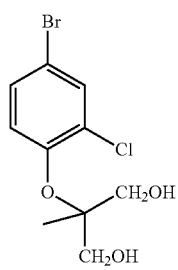

To a stirred solution of diethyl 2-(4-bromo-2-chlorophenoxy)-2-methylmalonate (18.9 g, 49.8 mmol) in MeOH (200 mL) was added NaBH$_4$ (15.1 g, 399 mmol) portionwise over 40 min at 0° C. The resulting mixture was warmed to rt and then heated to reflux for 1.5 h. The reaction mixture was cooled to rt and concentrated under reduced pressure. The residue was added water (300 mL) and extracted with EtOAc (3×200 mL). The combined extracts were dried over anhydrous Na$_2$SO$_4$, filtered, and concentrated under reduced pressure. The resulting residue was purified by flash column chromatography on silica gel eluting with 20% to 50% EtOAc/hexanes to afford title compound as a clear oil (13.5 g, 92%): ESI MS, m/z=317 [M+Na]$^+$.

Preparation of 3-(4-bromo-2-chlorophenoxy)-3-methyloxetane

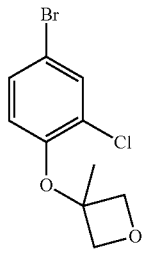

To a stirred solution of 2-(4-bromo-2-chlorophenoxy)-2-methylpropane-1,3-diol (13.5 g, 45.7 mmol) in anhydrous THF (200 mL) was added NaH (60%, 2.01 g, 50.3 mmol) portionwise at 0° C. under nitrogen. The reaction mixture was stirred for 40 min at 0° C. and then a solution of TsCl (9.15 g, 48.0 mmol) in anhydrous THF (20 mL) was added. The resulting mixture was stirred for 30 min at 0° C. After this time, NaH (60%, 2.01 g, 50.3 mmol) was added portionwise. The reaction mixture was then warmed to rt for 20 min and then heated to reflux for 2 h. After this time, the reaction mixture was cooled to rt and quenched by slow addition of ice cold water (10 mL). The resulting mixture was diluted with saturated $NH_4Cl$ aqueous solution (150 mL) and extracted with EtOAc (2×200 mL). The combined extracts were washed with brine (50 mL), dried over anhydrous $Na_2SO_4$, filtered, and concentrated under reduced pressure. The resulting residue was purified by flash column chromatography on silica gel eluting with 4% to 20% EtOAc/hexanes to afford title compound as a clear oil (6.41 g, 50%): $^1$H NMR (500 MHz, $CDCl_3$) δ 7.53 (d, J=2.4 Hz, 1H), 7.27-7.24 (m, 1H), 6.33 (d, J=8.7 Hz, 1H), 4.94 (d, J=6.7 Hz, 2H), 4.55 (d, J=7.3 Hz, 2H), 1.72 (s, 3H).

Preparation of 3-(2-chloro-4-iodophenoxy)-3-methyloxetane

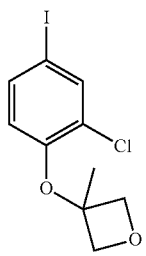

A stirred suspension of 3-(4-bromo-2-chlorophenoxy)-3-methyloxetane (5.78 g, 20.8 mmol), trans-cyclohexane-1,2-diamine (325 mg, 2.28 mmol), NaI (6.24 g, 41.6 mmol), and CuI (198 mg, 1.04 mmol) in anhydrous 1,4-dioxane (50 mL) was heated to reflux (115° C. oil bath) under nitrogen overnight. After this time, the reaction mixture was cooled to rt, diluted with EtOAc (50 mL) and hexanes (100 mL), and filtered. The filter cake was washed with EtOAc (50 mL). The filtrate was washed with saturated $NH_4Cl$ aqueous solution (2×100 mL), 20% $Na_2S_2O_3$ aqueous solution (100 mL), and brine (200 mL), dried over anhydrous $Na_2SO_4$, filtered, and concentrated under reduced pressure. The resulting residue was purified by flash column chromatography on silica gel eluting with 4% to 20% EtOAc/hexanes to afford title compound as a clear syrup (6.47 g, 96%): $^1$H NMR (300 MHz, $CDCl_3$) δ 7.70 (d, J=2.1 Hz, 1H), 7.43 (dd, J=8.6, 2.1 Hz, 1H), 6.19 (d, J=8.6 Hz, 1H), 4.95 (d, J=6.6 Hz, 2H), 4.57 (d, J=7.3 Hz, 2H), 1.74 (s, 3H).

Preparation of 5-bromo-1-chloro-3-fluoro-2-(methoxymethoxy)benzene

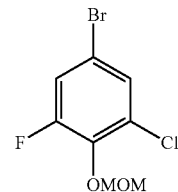

To a stirred mixture of 4-bromo-2-chloro-6-fluorophenol (6.00 g, 26.6 mmol) and $K_2CO_3$ (7.36 g, 53.3 mmol) in acetone (100 mL) was added MOMCl (4.24 g, 52.7 mmol) at 0° C. After the addition completed, the reaction mixture was warmed to rt and stirred overnight. The reaction mixture was then diluted with EtOAc (200 mL) and filtered. The filter cake was washed with EtOAc (100 mL). The filtrate was concentrated under reduced pressure. The resulting residue was triturated with 1:1 $CH_2Cl_2$/hexanes, filtered, and dried under high vacuum to afford compound 2 as a clear oil (7.26 g, >99%): $^1$H NMR (300 MHz, $CDCl_3$) δ 7.36-7.34 (m, 1H), 7.20 (dd, J=9.9, 2.3 Hz, 1H), 5.28 (s, 2H), 3.62 (s, 3H).

Preparation of 5-bromo-1-chloro-2-(methoxymethoxy)-3-((2-methylallyl)oxy)benzene and 5-bromo-1-chloro-2-(methoxymethoxy)-3-((2-methylprop-1-en-1-yl)oxy)benzene

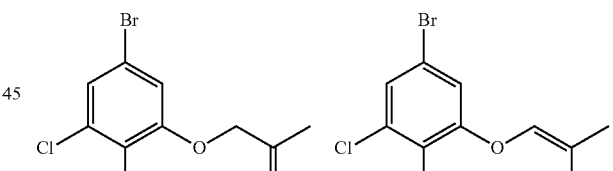

To a stirred solution of 2-methylprop-2-en-1-ol (3.86 g, 53.5 mmol) in anhydrous DMF (50 mL) was added NaH (60%, 2.13 g, 53.3 mmol) portionwise at 0° C. under nitrogen. The resulting mixture was stirred at 0° C. for 30 min. To the reaction mixture was added a solution of 5-bromo-1-chloro-3-fluoro-2-(methoxymethoxy)benzene [7.26 g (crude), 26.6 mmol (ca.)] in anhydrous DMF (8 mL). The resulting mixture was warmed to rt and stirred over weekend. After this time, the reaction mixture was quenched with ice cold water (200 mL), extracted with 1:1 EtOAc/hexanes (3×100 mL). The combined extracts were washed with 10% LiCl aqueous solution (2×50 mL) and brine (100 mL), dried over anhydrous $Na_2SO_4$, filtered, and concentrated under reduced pressure. The resulting residue was purified by flash column chromatography on silica gel eluting with 1% to 2% EtOAc/hexanes to afford a mixture of title compounds as a clear oil (7.45 g, 86%): $^1$H NMR (300

MHz, CDCl$_3$) δ 7.19 (d, J=2.3 Hz, 0.2H), 7.15 (d, J=2.2 Hz, 1H), 6.99 (d, J=2.3 Hz, 0.2H), 6.93 (d, J=2.2 Hz, 1H), 6.08 (s, 0.2H), 5.18 (s, 0.4H), 5.16 (s, 2H), 5.08 (s, 1H), 5.02 (s, 1H), 4.43 (s, 2H), 3.65 (s, 0.6H), 3.62 (s, 3H), 1.76 (s, 3H), 1.71 (s, 0.6H), 1.70 (s, 0.6H).

Preparation of 4-bromo-2-chloro-6-((2-methylallyl)oxy)phenol and 4-bromo-2-chloro-6-((2-methylprop-1-en-1-yl)oxy)phenol

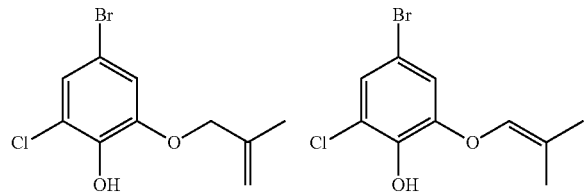

To a stirred solution of mixture of 5-bromo-1-chloro-2-(methoxymethoxy)-3-((2-methylallyl)oxy)benzene and 5-bromo-1-chloro-2-(methoxymethoxy)-3-((2-methylprop-1-en-1-yl)oxy)benzene (5:1, 7.45 g, 23.2 mmol) in THF (50 mL) was added an HCl solution in isopropanol (5 N, 23 mL, 115 mmol) at rt. The reaction mixture was stirred overnight. After this time, the reaction mixture was concentrated under reduced pressure. The resulting residue was purified by flash column chromatography on silica gel eluting with 5% to 10% EtOAc/hexanes to afford a mixture of title compounds (5:1) as a clear oil (6.17 g, 96%): $^1$H NMR (300 MHz, CDCl$_3$) δ 7.16-7.14 (m, 0.2H), 7.12-7.10 (m, 1H), 6.95-6.92 (m, 0.2H), 6.90-6.87 (m, 1H), 6.10 (s, 0.2H), 5.80 (s, 1H), 5.75 (s, 0.2H), 5.07-5.05 (m, 2H), 4.50 (s, 2H), 1.82 (s, 3H), 1.72-1.69 (m, 1.2H).

Preparation of 6-bromo-8-chloro-2,2-dimethyl-2,3-dihydrobenzo[b][1,4]dioxine

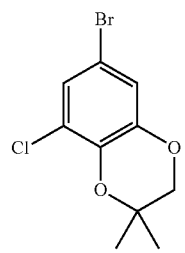

A solution of mixture of 4-bromo-2-chloro-6-((2-methylallyl)oxy)phenol and 4-bromo-2-chloro-6-((2-methylprop-1-en-1-yl)oxy)phenol (5:1, 6.17 g, 22.2 mmol) in HCO$_2$H (40 mL) was heated to reflux (120° C. oil bath) for 1.5 h. After this time, the reaction mixture was cooled to rt and concentrated under reduced pressure. The residue was diluted with CH$_2$Cl$_2$ (100 mL), cooled with ice/water bath, and basified by slow addition of saturated NaHCO$_3$ aqueous solution. The resulting mixture was filtered. The filter cake was washed with CH$_2$Cl$_2$ (100 mL). The filtrate layers were separated. The aqueous layer was back extracted with CH$_2$Cl$_2$ (2×30 mL). The combined organic layers were dried over anhydrous Na$_2$SO$_4$, filtered, and concentrated under reduced pressure. The resulting residue was purified by flash column chromatography on silica gel eluting with 2% to 6% EtOAc/hexanes to afford title compound as a light yellow oil (2.47 g, 40%): $^1$H NMR (300 MHz, CDCl$_3$) δ 7.09 (d, J=2.3 Hz, 1H), 6.96 (d, J=2.3 Hz, 1H), 3.89 (s, 2H), 1.38 (s, 6H).

Preparation of 8-chloro-6-iodo-2,2-dimethyl-2,3-dihydrobenzo[b][1,4]dioxine

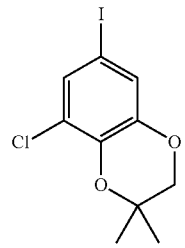

A stirred suspension of 6-bromo-8-chloro-2,2-dimethyl-2,3-dihydrobenzo[b][1,4]dioxine (2.47 g, 8.90 mmol), trans-cyclohexane-1,2-diamine (135 mg, 0.951 mmol), NaI (2.67 g, 17.8 mmol), and CuI (85 mg, 0.446 mmol) in anhydrous 1,4-dioxane (20 mL) was heated to reflux (115° C. oil bath) under nitrogen overnight. After this time, the reaction mixture was cooled to rt, diluted with EtOAc (20 mL) and hexanes (40 mL), and filtered. The filter cake was washed with EtOAc (20 mL). The filtrate was washed with saturated NH$_4$Cl aqueous solution (2×20 mL), 20% Na$_2$S$_2$O$_3$ aqueous solution (20 mL), and brine (40 mL), dried over anhydrous Na$_2$SO$_4$, filtered, and concentrated under reduced pressure. The resulting residue was purified by flash column chromatography on silica gel eluting with 2% EtOAc/hexanes to afford title compound as a light yellow oil (2.74 g, 95%): $^1$H NMR (300 MHz, CDCl$_3$) δ 7.25 (d, J=2.1 Hz, 1H), 7.13 (d, J=2.0 Hz, 1H), 3.89 (s, 2H), 1.39 (s, 6H).

Examples 22 and 23 are prepared as described in Representative Scheme 1 starting with an appropriately substituted aryl iodide.

Example 22

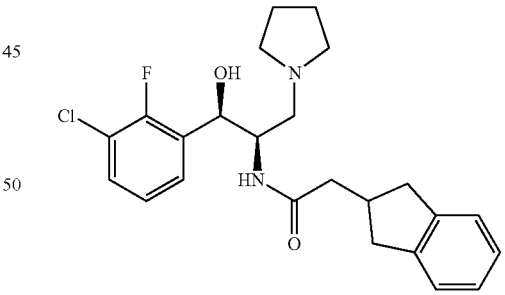

N-((1R,2R)-1-(3-chloro-2-fluorophenyl)-1-hydroxy-3-(pyrrolidin-1-yl)propan-2-yl)-2-(2,3-dihydro-1H-inden-2-yl)acetamide (Example 22)

$^1$H NMR (400 MHz, cdcl$_3$) δ 7.41 (t, J=6.9 Hz, 1H), 7.33 (t, J=6.9 Hz, 1H), 7.19-7.04 (m, 5H), 6.04 (d, J=7.8 Hz, 1H), 5.39 (s, 1H), 4.33-4.20 (m, 1H), 3.02-2.83 (m, 4H), 2.83-2.60 (m, 5H), 2.51 (dd, J=15.6, 6.7 Hz, 1H), 2.37 (dd, J=15.6, 6.7 Hz, 1H), 2.24 (qd, J=14.1, 7.5 Hz, 2H), 1.88-1.72 (m, 4H); HRMS (ESI) m/z: Calcd for [M+H]+ 431.1902; Found: 431.1887.

Example 23

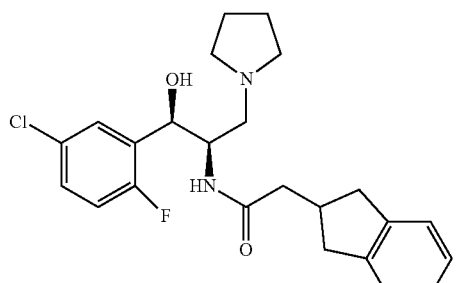

N-((1R,2R)-1-(5-chloro-2-fluorophenyl)-1-hydroxy-3-(pyrrolidin-1-yl)propan-2-yl)-2-(2,3-dihydro-1H-inden-2-yl)acetamide (Example 23)

$^1$H NMR (400 MHz, cdcl$_3$) δ 7.51 (dd, J=6.3, 2.7 Hz, 1H), 7.25-7.09 (m, 5H), 6.97 (t, J=9.2 Hz, 1H), 5.97 (d, J=8.0 Hz, 1H), 5.33 (s, 1H), 4.29 (m, 1H), 3.00 (dd, J=15.5, 7.3 Hz, 2H), 2.91-2.82 (m, 2H), 2.72 (m, 5H), 2.50 (dd, J=15.7, 6.7 Hz, 1H), 2.40 (dd, J=15.5, 6.5 Hz, 1H), 2.34-2.16 (m, 2H), 1.80 (m, 4H); HRMS (ESI) m/z: Calcd for [M+H]$^+$ 431.1902; Found: 431.1891.

Representative Scheme 2

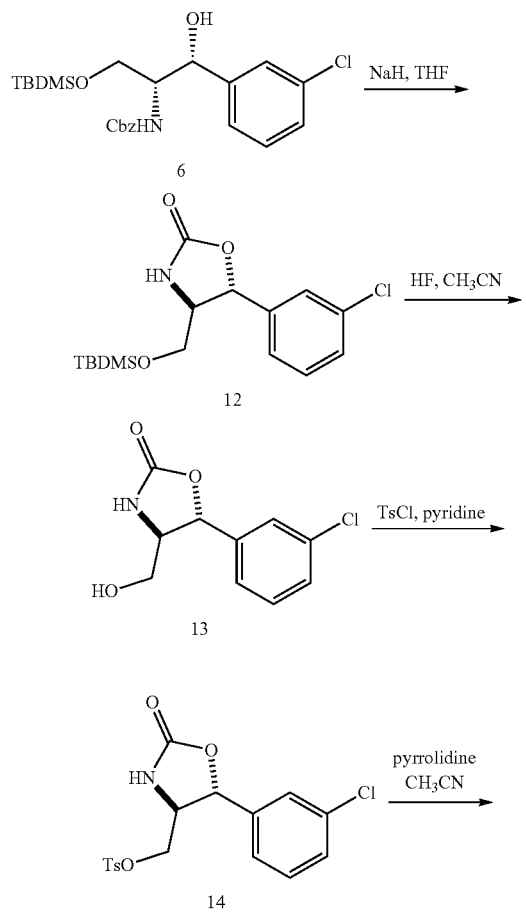

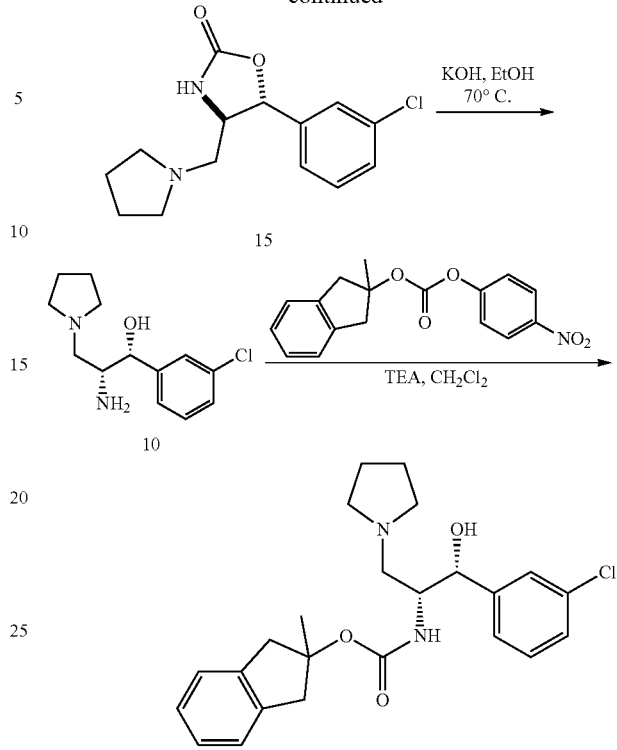

Example 14

(4R,5R)-4-(((tert-butyldimethylsilyl)oxy)methyl)-5-(3-chlorophenyl)oxazolidin-2-one (12)

To a solution of benzyl ((1R,2R)-3-((tert-butyldimethylsilyl)oxy)-1-(3-chlorophenyl)-1-hydroxypropan-2-yl)carbamate 6 (2.00 g, 4.44 mmol) in THF (20 mL) at room temperature was added 60% NaH dispersion in oil (210 mg, 5.33 mmol). The reaction stirred at room temperature for 2 h. The reaction was quenched with the addition of saturated aqueous ammonium chloride solution, diluted with water, and extracted 2× with ethyl acetate. The combined organic layers were dried over magnesium sulfate, filtered, and concentrated. The crude residue was purified by flash chromatography eluting with 0-50% EtOAc in Hexanes to afford the title compound as a colorless oil which solidified upon standing. (1.21 g, 80%)

(4R,5R)-5-(3-chlorophenyl)-4-(hydroxymethyl)oxazolidin-2-one (13)

To a solution of (4R,5R)-4-(((tert-butyldimethylsilyl)oxy)methyl)-5-(3-chlorophenyl)oxazolidin-2-one 12 (1.00 g, 2.92 mmol) in acetonitrile (20 mL) was added 48% aqueous HF (1.80 mL, 49.7 mmol). After 1 h, the reaction mixture was concentrated and purified by column chromatography eluting with 0-10% methanol in dichloromethane to afford the title compound as a clear, colorless oil. (606 mg, 91%)

((4R,5R)-5-(3-chlorophenyl)-2-oxooxazolidin-4-yl)methyl 4-methylbenzenesulfonate (14)

To a solution of (4R,5R)-5-(3-chlorophenyl)-4-(hydroxymethyl)oxazolidin-2-one 13 (426 mg, 1.87 mmol) in pyridine (2.5 mL) was added 4-methylbenzenesulfonyl chloride (535 mg, 2.81 mmol). The reaction stirred at room temperature for 5 h, then was concentrated. The crude residue was purified by column chromatography eluting with 0-10% methanol in dichloromethane to afford the title compound which was crystallized from dichloromethane/hexanes to give the title compound as a white solid. (457 mg, 64%).

(4R,5R)-5-(3-chlorophenyl)-4-(pyrrolidin-1-ylmethyl)oxazolidin-2-one (15)

To a solution of ((4R,5R)-5-(3-chlorophenyl)-2-oxooxazolidin-4-yl)methyl 4-methylbenzenesulfonate (591 mg, 1.55 mmol) in acetonitrile (8 mL) was added pyrrolidine (0.64 mL, 7.7 mmol). The reaction was fitted with a reflux condenser, heated to 75° C. and stirred for 4 h. The reaction was concentrated. The crude residue was purified by column chromatography eluting with 0-10% methanol in dichloromethane to afford the title compound as a colorless film which solidified upon standing. (327 mg, 75%)

(1R,2R)-2-amino-1-(3-chlorophenyl)-3-(pyrrolidin-1-yl)propan-1-ol (10)

To a solution of (4R,5R)-5-(3-chlorophenyl)-4-(pyrrolidin-1-ylmethyl)oxazolidin-2-one 15 (272 mg, 0.969 mmol) in ethanol (5.0 mL) was added potassium hydroxide (2 mL of a 2M aqu. solution, 4.84 mmol). The reaction was heated in a sealed tube at 70° C. for 16 h. The reaction was cooled to room temperature then diluted with dichloromethane and washed with water and brine. The organic layer was dried over magnesium sulfate, filtered, and concentrated. The crude residue was purified by column chromatography eluting with 3-7% (7N $NH_3$ in methanol)/dichloromethane to afford the title compound as a clear, colorless gum. (211 mg, 86%)

2-methyl-2,3-dihydro-1H-inden-2-yl ((1R,2R)-1-(3-chlorophenyl)-1-hydroxy-3-(pyrrolidin-1-yl)propan-2-yl)carbamate (Example 14)

To a solution of (1R,2R)-2-amino-1-(3-chlorophenyl)-3-(pyrrolidin-1-yl)propan-1-ol 10 (50 mg, 0.20 mmol) in dichloroethane (1.5 mL) was added 2-methyl-2,3-dihydro-1H-inden-2-yl (4-nitrophenyl) carbonate (prepared from 2-methyl-2-indanol as described below for 2,3-dihydro-1H-inden-2-yl (4-nitrophenyl) carbonate) (80 mg, 0.26 mmol) followed by triethylamine (54 uL, 0.39 mmol). The reaction was heated to 60° C. for 16 h. Another 30 mg of 2-methyl-2,3-dihydro-1H-inden-2-yl (4-nitrophenyl) carbonate (prepared as described for 2,3-dihydro-1H-inden-2-yl (4-nitrophenyl) carbonate below) (30 mg, 0.96 mmol) was added along with additional triethylamine (50 uL, 0.33 mmol). After 4 h, the reaction was diluted with dichloromethane and washed with brine. The organic layer was dried over magnesium sulfate, filtered, and concentrated. The crude residue was purified by column chromatography eluting with 0-10% methanol in dichloromethane to give the title compound as an amorphous solid (24 mg, 29%). $^1$H NMR (400 MHz, Chloroform-d) δ 7.36 (s, 1H), 7.29-7.19 (m, 2H), 7.17-7.15 (m, 5H), 5.08-4.98 (m, 1H), 4.89 (d, J=8.6 Hz, 1H), 3.99 (m, 1H), 3.31 (dd, J=41.2, 16.5 Hz, 2H), 3.06 (dd, J=16.4, 10.9 Hz, 2H), 2.84 (ddd, J=41.6, 12.9, 5.1 Hz, 2H), 2.67 (m, 4H), 1.72 (brs, 4H), 1.56 (s, 3H); HRMS (ESI) m/z: Calcd for [M+H]$^+$ 429.1945; Found: 429.1939.

Preparation of 2,3-dihydro-1H-inden-2-yl (4-nitrophenyl) carbonate

To a stirred solution of 2-indanol (1.34 g, 10 mmol) in anhydrous $CH_2Cl_2$ (50 mL) was added 4-nitrophenyl chloroformate (2.01 g, 10 mmol) followed by a solution of pyridine (0.81 mL, 10 mmol) in anhydrous $CH_2Cl_2$ (10 mL) under nitrogen at 0° C. After the addition completed, the reaction mixture was warmed to rt and stirred overnight. The reaction mixture was then concentrated under reduced pressure. The residue was dissolved in EtOAc (50 mL), washed with 10% citric acid aqueous solution (2×40 mL) and brine (40 mL), dried over anhydrous $Na_2SO_4$, filtered, concentrated under reduced pressure. The residue was further triturated with EtOAc and dried under high vacuum to provide compound 3 as an off-white solid (1.17 g, 39%): $^1$H NMR (500 MHz, CDCl$_3$) δ 8.29-8.26 (m, 2H), 7.39-7.21 (m, 6H), 5.59-5.55 (m, 1H), 3.41 (dd, J=17.0, 6.5 Hz, 2H), 3.20 (dd, J=17.0, 2.5 Hz, 2H).

The following compounds were prepared as in Scheme 2 starting with the requisite aryl iodide, amine and 4-nitrophenyl carbonate.

2,3-dihydro-1H-inden-2-yl ((1R,2R)-1-(3-chloro-4-cyclopropoxyphenyl)-1-hydroxy-3-(pyrrolidin-1-yl)propan-2-yl)carbamate (Example 12)

$^1$H NMR (500 MHz, CDCl$_3$) δ 7.33-7.15 (m, 7H), 5.40-5.37 (m, 1H), 5.07 (s, 1H), 5.02 (br s, 1H), 4.05 (br s, 1H), 3.80-3.77 (m, 1H), 3.30-2.60 (m, 10H), 1.89 (br s, 4H), 0.85-0.75 (m, 4H); ESI MS, m/z=471 [M+H]$^+$.

2,3-dihydro-1H-inden-2-yl ((1R,2R)-1-(3-chlorophenyl)-1-hydroxy-3-(pyrrolidin-1-yl)propan-2-yl)carbamate (Example 6)

$^1$H NMR (500 MHz, CDCl$_3$) δ 7.34 (s, 1H), 7.23-7.04 (m, 7H), 6.80 (bs, 1H), 5.40-5.37 (m, 1H), 5.03 (s, 1H), 4.89-4.87 (m, 1H), 4.02 (bs, 1H), 3.27-3.18 (m, 2H), 2.97-2.93 (m, 1H), 2.88-2.55 (m, 7H), 1.79 (bs, 4H); ESI MS, m/z=415 [M+H]$^+$.

2,3-dihydro-1H-inden-2-yl ((1R,2R)-1-(3-chlorophenyl)-3-((R)-3-fluoropyrrolidin-1-yl)-1-hydroxypropan-2-yl)carbamate oxalate (Example 15)

$^1$H NMR (400 MHz, DMSO-d$_6$) δ 7.37-7.07 (m, 8H), 6.80 (d, J=9.4 Hz, 1H), 5.33 (d, J=54.4 Hz, 1H), 5.13 (m, 1H), 4.75 (br s, 1H), 3.98 (m, 1H), 3.39-2.51 (m, 10H), 2.31-1.90 (m, 2H); HRMS (ESI) m/z: Calcd for [parent+H]$^+$ 433.1694; Found: 433.1683.

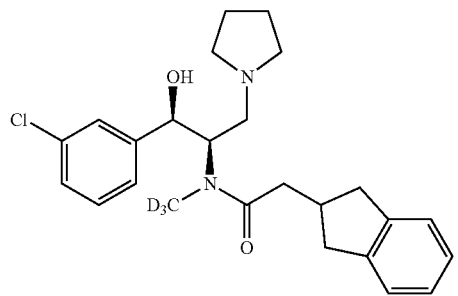 [SMILES: [2H]C([2H])([2H])N(C(=O)CC1Cc2ccccc2C1)[C@H](CN1CCCC1)[C@H](O)c1cccc(Cl)c1]

N-((1R,2R)-1-(3-chlorophenyl)-1-hydroxy-3-(pyrrolidin-1-yl)propan-2-yl)-2-(2,3-dihydro-1H-inden-2-yl)-N-(methyl-d3)acetamide (Example 17)

Prepared as in Scheme 2 using (4R,5R)-4-(((tert-butyldimethylsilyl)oxy)methyl)-5-(3-chlorophenyl)-3-(methyl-d3)oxazolidin-2-one in place of compound 12, synthesis shown below.

$^1$H NMR (400 MHz, CDCl$_3$)(peaks for major rotamer reported) 7.38 (t, J=1.9 Hz, 1H), 7.25-7.16 (m, 5H), 7.16-7.10 (m, 2H), 4.93 (d, J=5.2 Hz, 1H), 3.18-3.07 (m, 2H), 3.02-2.70 (m, 3H), 2.68-2.47 (m, 7H), 2.38-2.30 (m, 2H), 1.84-1.71 (m, 4H). 6 HRMS (ESI) m/z: Calcd for [M+H]$^+$ 430.2341; Found: 430.2327.

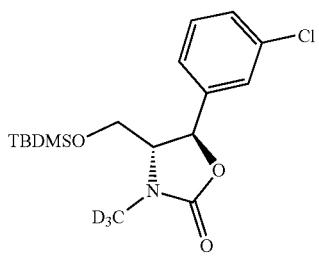 [SMILES: [2H]C([2H])([2H])N1C(=O)O[C@H](c2cccc(Cl)c2)[C@H]1CO[Si](C)(C)C(C)(C)C]

(4R,5R)-4-(((tert-butyldimethylsilyl)oxy)methyl)-5-(3-chlorophenyl)-3-(methyl-d3)oxazolidin-2-one To a solution of (4R,5R)-4-(((tert-butyldimethylsilyl)oxy)methyl)-5-(3-chlorophenyl)oxazolidin-2-one (1.20 g, 3.51 mmol) in DMF (15 mL) at 0° C. was added sodium hydride (60% oil disp) (0.21 g, 5.26 mmol) slowly. After stirring for 1 h, iodomethane-d3 (2.54 g, 1.10 mL, 5 Eq, 17.5 mmol) was added. After 2 h, the reaction was quenched with the addition of saturated ammonium chloride solution and extracted with dichloromethane 3×. The combined organic layers were dried over magnesium sulfate, filtered, and concentrated. Purified by column chromatography eluting with 0-50% ethyl acetate in hexanes. Isolated the title compound as a clear colorless oil which solidified upon standing (1.27 g, 100%).

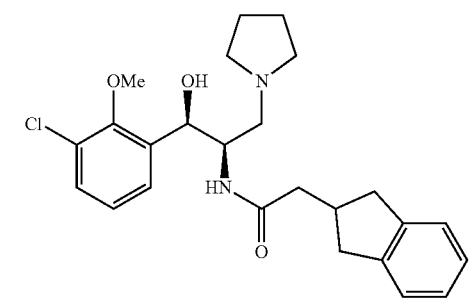 [SMILES: COc1c(Cl)cccc1[C@@H](O)[C@@H](CN1CCCC1)NC(=O)CC1Cc2ccccc2C1]

N-((1R,2R)-1-(3-chloro-2-methoxyphenyl)-1-hydroxy-3-(pyrrolidin-1-yl)propan-2-yl)-2-(2,3-dihydro-1H-inden-2-yl)acetamide (Example 18)

$^1$H NMR (400 MHz, CDCl$_3$) δ 7.40 (dd, J=7.8, 1.6 Hz, 1H), 7.31 (dd, J=8.0, 1.6 Hz, 1H), 7.16-7.09 (m, 4H), 7.06 (t, J=7.8, 6.9 Hz, 1H), 6.32 (d, J=7.6 Hz, 1H), 5.36 (d, J=2.8 Hz, 1H), 4.33 (m, 1H), 3.92 (s, 3H), 2.99-2.84 (m, 4H), 2.85-2.69 (m, 5H), 2.51 (dd, J=15.5, 6.9 Hz, 1H), 2.40 (dd, J=15.6, 6.9 Hz, 1H), 2.34-2.15 (m, 2H), 1.93-1.74 (m, 4H).

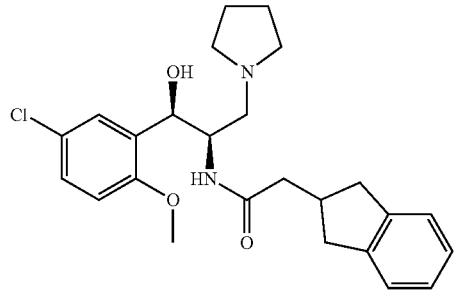 [SMILES: COc1ccc(Cl)cc1[C@@H](O)[C@@H](CN1CCCC1)NC(=O)CC1Cc2ccccc2C1]

N-((1R,2R)-1-(5-chloro-2-methoxyphenyl)-1-hydroxy-3-(pyrrolidin-1-yl)propan-2-yl)-2-(2,3-dihydro-1H-inden-2-yl)acetamide (Example 19)

Prepared as in Scheme 2 using 4-chloro-2-iodo-1-methoxybenzene.

$^1$H NMR (400 MHz, CDCl$_3$) δ 7.45 (d, J=2.7 Hz, 1H), 7.23-7.04 (m, 5H), 6.75 (d, J=8.7 Hz, 1H), 6.39 (d, J=8.3 Hz, 1H), 5.40-5.34 (m, 1H), 4.54-4.42 (m, 1H), 3.82 (s, 3H), 3.32-3.05 (m, 6H), 2.90 (dd, J=15.6, 7.5 Hz, 1H), 2.81-2.58 (m, 2H), 2.45 (dd, J=15.6, 7.1 Hz, 1H), 2.38-2.30 (m, 2H), 2.30-2.15 (m, 2H), 2.08-1.94 (m, 4H). HRMS (ESI) m/z: Calcd for [M+H]$^+$ 443.2102; Found: 443.2087.

The following compound was prepared as in Representative Scheme 2 using a non-commercial aryl iodide in place of compound 4. The synthesis of this iodide is included below.

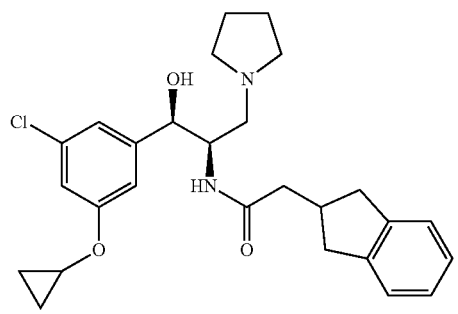 [SMILES: O=C(CC1Cc2ccccc2C1)N[C@H](CN1CCCC1)[C@H](O)c1cc(Cl)cc(OC2CC2)c1]

N-((1R,2R)-1-(3-chloro-5-cyclopropoxyphenyl)-1-hydroxy-3-(pyrrolidin-1-yl)propan-2-yl)-2-(2,3-dihydro-1H-inden-2-yl)acetamide (Example 20)

Prepared as in Scheme 2 using 1-chloro-3-cyclopropoxy-5-iodobenzene.

$^1$H NMR (400 MHz, CDCl$_3$) δ 7.13 (m, 4H), 6.98 (m, 2H), 6.89 (m, 1H), 5.95 (d, J=7.6 Hz, 1H), 5.00 (d, J=2.8 Hz, 1H), 4.22 (m, 1H), 3.67 (m, 1H), 2.97 (dd, J=15.6, 7.7 Hz, 1H), 2.92-2.82 (m, 3H), 2.82-2.56 (m, 5H), 2.50 (dd, J=15.6, 6.8 Hz, 1H), 2.36 (dd, J=15.5, 6.6 Hz, 1H), 2.32-2.13 (m, 2H), 1.78 (m, 4H), 0.74 (m, 4H). HRMS (ESI) m/z: Calcd for [M+H]$^+$ 469.2258; Found: 469.2241.

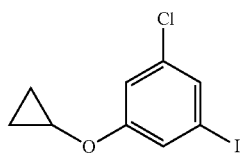 [SMILES: Clc1cc(I)cc(OC2CC2)c1]

1-chloro-3-cyclopropoxy-5-iodobenzene

To a solution of 3-chloro-5-iodophenol (1.2 g, 4.7 mmol) in N,N-dimethylacetamide (15 mL) was added cesium carbonate (6.40 g, 19.6 mmol) and bromocyclopropane (2.6 mL, 33 mmol). The reaction was heated at 150° C. overnight in a sealed tube. After 24 h, an additional 1.5 mL of bromocyclopropane was added and the reaction was stirred for 24 h. The reaction was cooled to room temperature, poured into water and extracted with ethyl acetate. The organic layer was dried over magnesium sulfate, filtered, and concentrated. The reaction mixture was purified by column chromatography eluting with 0-50% ethyl acetate in hexanes. The title compound was isolated as a clear colorless liquid (646 mg, 47%).

GCS Inhibition

GCS inhibitors are known. Some GCS inhibitors, e.g., eliglustat and miglustat, possess sufficient activity to inhibit GCS activity, and therefore have been proposed as suitable for treating diseases related to glycolipid accumulation. Unfortunately, these compounds and/or their pharmacological profile are not completely satisfactory. For example, miglustat is capable of crossing the blood brain barrier (BBB), but does not achieve levels in the CNS that exceed its $IC_{50}$ and many of its effects are either off target or due to its potential activity as a chemical chaperone for beta-glucocerebrosidase. Eliglustat has greater potency than miglustat at inhibiting GCS, but cannot cross the BBB. Accordingly diseases which require a therapeutic drug to cross the BBB by cannot be treated. Consequently, there is an ongoing need to provide new compounds that effectively and selectively inhibit GCS, and, in some embodiments, are capable of crossing the BBB. Compounds of structural formula (I) exhibit these beneficial properties.

To demonstrate the ability of the present GCS inhibitors to reduce glycolipid accumulation in lysosomes and to cross the BBB, compounds of the invention were prepared and assayed. Compounds of structural formula (I) also are more potent GCS inhibitors in cells and exhibit an improved metabolic stability compared to prior GCS inhibitors.

The compounds were screened for inhibition of GCS in broken cell and whole cell assays, and for MDR1 substrate recognition. Compounds of structural formula (I) were found to inhibit GCS at low nanomolar concentrations with little to no apparent recognition by MDR1. In addition, intraperitoneal administration of a present compound to mice for 3 days resulted in a significant dose dependent decrease in brain glucosylceramide content, an effect not seen in mice dosed in parallel with eliglustat tartrate.

The compounds of structural formula (I) retain activity against GCS and eliminate substrate specificity for the MDR1 protein. As a result, novel compounds that inhibit GCS in both the brain and peripheral organs have been provided.

Assays

Materials

N-((1R,2R)-1-(2,3-dihydrobenzo-[b][1,4]dioxin-6-yl)-1-hydroxy-3-(pyrrolidin-1-yl)propan-2-yl)octanamide (eliglustat tartrate) was provided by Genzyme Corporation. [$^3$H]Vinblastine and [$^{14}$C]mannitol were purchased from American Radiolabeled Chemicals (St Louis, Mo.).

GCS Inhibition in MDCKII Cells

Parental (WT-)MDCKII cells were routinely maintained in medium consisting of Opti-MEM/F12 (1:1), 5% FBS, 100 U/mL of penicillin, 100 µg/mL streptomycin and 200 mM L-glutamine. MDCKII cells were newly thawed from frozen ampules every two months.

Stock solutions of water-insoluble glycosphingolipid inhibitors (100 mM) were prepared by dissolving each inhibitor into 100% ethanol as previously described (3). The inhibitor-ethanol solutions then were diluted 50× into 2 mM delipidated bovine serum albumin-phosphate buffered saline solution to make water-soluble glycosphingolipid inhibitor-bovine serum albumin complexes. The inhibitor-bovine serum album complexes were sterile-filtered and stored at −20° C. Prior to use, portions of the inhibitor-bovine serum albumin complexes were further diluted with Opti-F12 to make treatment solutions. Equal amounts of bovine serum albumin and ethanol were added into the control cultures. Cells ($5\times10^5$) were seeded into 10-cm culture dishes containing 10 ml of Opti-F12 with 5% FBS. After 24 hours, the medium was replaced with fresh serum-free Opti-F12 medium, and cells were exposed to candidate GCS inhibitors at concentrations of 0, 1, 3, 10, 30, 100 and 300 nM for 24 hours.

Cell Lipid Analysis

Following inhibitor treatment, whole cellular lipids of wild type MDCKII cells were extracted as previously described in detail (10). Briefly, cells were washed with ice-cold phosphate buffered saline, fixed by methanol, and collected with rubber scraper. Chloroform was then added to yield a theoretical ratio of chloroform:methanol:water at 1:2:0.8 (v/v/v) to form a mono-phase. Cell debris and proteins were removed by centrifugation at 2200×g for 30 min. The supernatants were portioned by adding chloroform and 0.9% NaCl. The lower organic phases containing neutral glycosphingolipids lipids were washed with methanol and 0.9% NaCl, and subjected to base- and acid-hydrolysis (10). A portion of purified glycosphingolipids normalized to 100 nmol of total phospholipids was analyzed by high performance thin layer chromatography. The thin layer chromatography separations were processed twice. The plate pre-treated with 1% sodium borate was first developed in a solvent system consisting of chloroform/methanol (98/2, v/v). After air drying, the plate was then developed in a solvent system containing chloroform/methanol/water (70/30/4, v/v/v). The levels of glucosylceramide were detected by charring with 8% cupric sulfate in 8% phosphoric acid, and quantified by densitometric scanning using ImageJ, NIH Image. Image data was analyzed, and the $IC_{50}$ of each inhibitor was calculated using GraphPad Prism (version 5.03).

Reduction of Brain Glucosylceramide and Glucosylsphingosine in CBE Mice

The reduction by inhibitors of GCS in brain glucosylceramide and glucosylsphingosine content was determined by the use of mice with Gba 1 mutant alleles, termed D409V/null. These are knock-in mice with a Gba 1 point mutation encoding Valine (V) 409 for the wild type (WT) Aspartate (D) on one missense allele and a null heteroallele [D409V/ null (9V/null)]. The D409V/null and WT littermates were of mixed gender and mixed, but matched, genetic backgrounds of C57BL/129Sv/FVB. (Xu Y H, Sun Y, Barnes S, Grabowski G A (2010) Comparative therapeutic effects of velaglucerase alfa and imiglucerase in a Gaucher disease mouse model. PLoS One 5: e10750.) Mice were treated with intraperitoneal conduritol B epoxide (CBE), an irreversible inhibitor of beta-glucocerebrosidase (25 mg/kg/day) for all groups beginning at post-partum day 15. Mice were concurrently treated with GCS inhibitor or vehicle control for 14 days. The mice were sacrificed 2 hours following the last injection and tissues including brain, liver, spleen, kidney and lung were analyzed for glucosylceramide and glucosylsphingosine by mass spectrometry.

Mouse Tissue Lipid Analysis

Lipid extractions of liver, kidney, and brain were performed as previously described (7). Briefly, frozen liver (about 0.5 g), two kidneys (about 0.3 g) and whole brain (about 0.4 g) were individually homogenized in sucrose buffer (250 mM sucrose, pH 7.4, 10 mM HEPES and 1 mM EDTA), at 0.2 g tissue/1 mL of sucrose buffer, with a Tri-R homogenizer. Each 0.8 mL of homogenate was mixed with 2 mL of methanol and 1 mL of chloroform, bath sonicated for 1 min and incubated at room temperature for 1 h. Tissue debris were removed by centrifugation at 2,400× gravity for 30 min. The pellets were re-extracted by mixing with 1 mL of methanol, 0.5 mL of chloroform and 0.4 mL of 0.9% NaCl (chloroform/methanol/0.9% NaCl, 1:2:0.8), incubated at room temperature for 1 h and centrifuged at 2,400× gravity for another 30 min. Two extracts were combined and mixed with 4.5 mL of chloroform and 1.2 mL of 0.9% NaCl (chloroform/methanol/0.9% NaCl, 2:1:0.8). After centrifugation at 800× gravity for 5 min, lower layer was washed with 3 mL of methanol and 2.4 mL of 0.9% NaCl. Second washing was carried with 3 mL of methanol, 2 mL of water and 0.4 mL of 0.9% NaCl followed by a 5 min centrifugation at 800× gravity. The resultant lower phase was collected and dried under a stream of $N_2$ gas.

The analysis of neutral glycosphingolipids from mouse liver, kidney, and brain was processed after alkaline methanolysis. Kidney lipids were incubated with 2 mL of chloroform and 1 ml of 0.21N NaOH in methanol for 2 h (kidney) or 7.5 h (liver and brain) at RT. The lipid extract was normalized to 0.5 μmol of total phospholipid phosphate (liver and kidney) or 2 μmol of total phospholipid phosphate (brain) for high performance thin layer chromatography analysis. After alkaline methanolysis, the brain lipids were passed through a silica gel column (7). Borate-impregnated thin layer chromatography plates were developed in a two solvent system. Plates were first developed in chloroform/methanol (98:2, v/v). The plates loaded with kidney and liver lipids were then developed in chloroform/methanol/water (64:24:4, v/v/v), and brain lipids were further separated in chloroform/methanol/water (60:30:6, v/v/v). GlcCer levels were quantified by comparison to known standards.

Assay Results

The activity of compounds of structural formula (I) at inhibiting GlcCer production in the broken cell assay is summarized in Table 1.

TABLE 1

| Example | MDCK IC50[a] (nM) | MLM T½[b] (min) | IP PK Plasma AUC[c] (ng*hr/mL) | IP PK Brain AUC[c] (ng*hr/mL) | Reduction in brain GlcCer in CBE mice[d] (dose in μmol/kg/day) |
|---|---|---|---|---|---|
| 1 | 1.0 | 18 | 1539 | 1109 | 23% (36) |
| 2 | 0.081 | 170 | 1989 | 1316 | 21% (26) |
| 3 | 4.1 | 316 | | | |
| 4 | 0.14 | 24 | 1021 | 293 | 33% (26) |
| 5 | 0.74 | 40 | 849 | 366 | 64% (100) |
| 6 | 3.8 | 18 | 401 | 997 | NC (26) |
| 7 | 0.061 | 44 | 590 | 129 | 49% (26) |
| 8 | 0.54 | 91 | | | |
| 9 | 0.8 | 50 | 2182 | 869 | 43% (26) |
| 10 | 8.7 | 12 | 289 | 940 | |
| 11 | 0.63 | 5.5 | 397 | 178 | NC (26) |
| 12 | 0.32 | 29 | 370 | 210 | 32% (26) |
| 13 | 0.71 | 187 | 535 | 216 | NC (26) |
| 14 | 9.2 | | 324 | | |
| 15 | 19.5 | 0.8 | 913 | 2656 | |
| 16 | 6.8 | 54 | | | |
| 17 | 11 | 15 | 366 | 742 | |
| 18 | 81.5 | | | | |
| 19 | 0.43 | 7.1 | | | |
| 20 | 2.1 | 6.5 | | | |
| 21 | 24.1 | >1000 | | | |
| 22 | 141 | 4.6 | | | |
| 23 | 0.17 | 24 | 644 | BLQ | |

[a] Inhibition of GlcCer production in whole wild-type MDCKII cells. [b] Half-life when incubated with mouse liver microsomes. [c] Areas under the drug concentration curve after single IP dose in mice (10 mg/kg). [d] Reduction in brain levels of glucosylceramide in CBE mice after 14 days of qd dosing with test drug administered IP. NC=no change.

The following is the structure of the control compound used in all tests and assays disclosed herein.

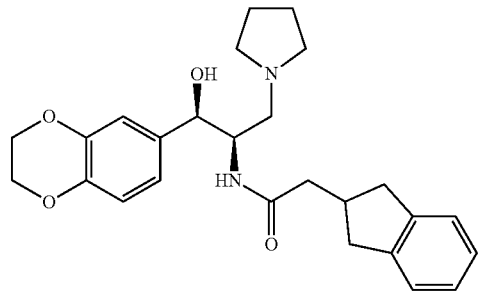 [SMILES: O=C(CC1Cc2ccccc2C1)N[C@H](CN1CCCC1)[C@H](O)c1ccc2c(c1)OCCO2]

In accordance with the present invention, it has been discovered that the chloro substituent at the 3-position of the phenyl ring results in an unexpected potency for the compound of structural formula (I) with respect to an MDCK IC50 inhibitor. As shown in the following Table 2, compounds of structural formula (I), having a chloro-substituent at the 3-position of the phenyl ring, were compared to identical compounds lacking the 3-chloro substituent. Typically, an at least 10-fold improvement was demonstrated.

It has also been discovered that the chloro substituent at the 3-position generally imparts greater metabolic stability, as indicated by MLM T1/2 in Table 2, as well as improved drug exposure in the brain (Examples 5 and 7 in Table 2).

TABLE 2

Impact of Cl vs H on activity and liver microsomal stability for various $R^1$

| Example | Structure | MDCK IC50 (nM) | MLM T½ (min) | No. | Structure | MDCK IC50 (nM) | MLM T½ (min) |
|---|---|---|---|---|---|---|---|
| Ex. 1 | (3-Cl, R¹ on 4-position) | 1.0 | 18 | Comp. Ex. 1 | (3-H, R¹ on 4-position) | 6.5 | 15 |
| Ex. 2 | (3-Cl, 4-OtBu) | 0.081 | 170 | Comp. Ex. 2 | (3-H, 4-OtBu) | 2.5 | 120 |

TABLE 2-continued

Impact of Cl vs H on activity and liver microsomal stability for various $R^1$

| Example | Structure | MDCK IC50 (nM) | MLM T½ (min) | No. | Structure | MDCK IC50 (nM) | MLM T½ (min) |
|---|---|---|---|---|---|---|---|
| Ex. 3 | (structure with Cl, $R^1$) | 4.1 | 316 | Comp. Ex. 3 | (structure with H, $R^1$) | 3.6 | 251 |
| Ex. 4 | (structure with Cl, OCF$_3$) | 0.14 | 24 | Comp. Ex. 4 | (structure with H, O-cyclopropyl) | 1.7 | 3.8 |

TABLE 2-continued

Impact of Cl vs H on activity and liver microsomal stability for various R¹

| Example | Structure | MDCK IC50 (nM) | MLM T½ (min) | No. | Structure | MDCK IC50 (nM) | MLM T½ (min) |
|---|---|---|---|---|---|---|---|
| Ex. 5 | 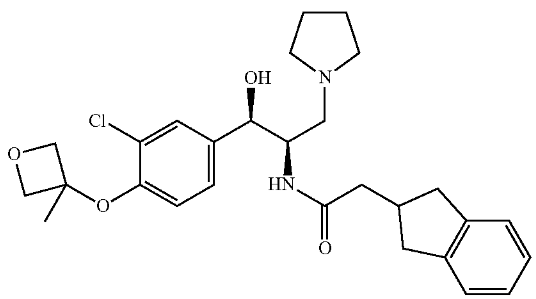 [SMILES: CC1(Oc2ccc([C@@H](O)[C@@H](CN3CCCC3)NC(=O)CC3Cc4ccccc4C3)cc2Cl)COC1] | 0.74 | 40 | Comp. Ex. 5 | 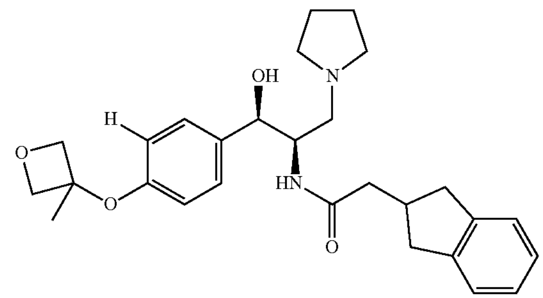 [SMILES: CC1(Oc2ccc([C@@H](O)[C@@H](CN3CCCC3)NC(=O)CC3Cc4ccccc4C3)cc2)COC1] | 7.9 | 24 |
| Ex. 7 | 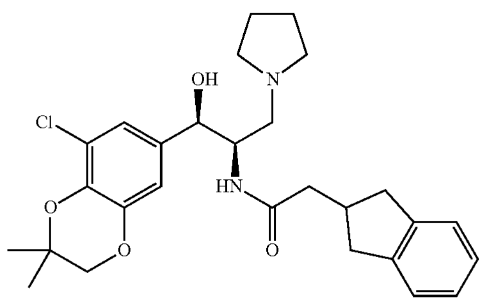 [SMILES: CC1(C)COc2cc([C@@H](O)[C@@H](CN3CCCC3)NC(=O)CC3Cc4ccccc4C3)cc(Cl)c2O1] | 0.061 | 44 | Comp. Ex. 7 | 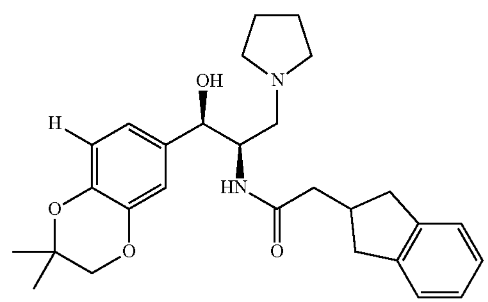 [SMILES: CC1(C)COc2cc([C@@H](O)[C@@H](CN3CCCC3)NC(=O)CC3Cc4ccccc4C3)ccc2O1] | 1.0 | 29 |

TABLE 2-continued

Impact of Cl vs H on activity and liver microsomal stability for various R¹

| Example | Structure | MDCK IC50 (nM) | MLM T½ (min) | No. | Structure | MDCK IC50 (nM) | MLM T½ (min) |
|---|---|---|---|---|---|---|---|
| Ex. 8 | (Cl, R¹) | 0.54 | 91 | Comp. Ex. 8 | (H, R¹) | 3.9 | 56 |
| Ex. 13 | (Cl, cyclopropyl) | 0.71 | 187 | Comp. Ex. 9 | (H, OCHF₂) | 9.6 | 38 |

TABLE 2-continued

Impact of Cl vs H on activity and liver microsomal stability for various $R^1$

| Example | Structure | MDCK IC50 (nM) | MLM T½ (min) | No. | Structure | MDCK IC50 (nM) | MLM T½ (min) |
|---|---|---|---|---|---|---|---|
| Ex. 19 | [structure with Cl and $R^1$ substituents, pyrrolidine, OH, indane] | 0.43 | | Comp. Ex. 19 | [structure with H and $R^1$ substituents, pyrrolidine, OH, indane] | 4.8 | |
| | [structure with Cl, OMe substituents] | | | | [structure with H, OMe substituents] | | |

Methods and Compositions

The present invention provides GCS inhibitors, as exemplified by compounds of structural formula (I), for the treatment of a variety of diseases and conditions wherein inhibition of GCS has a beneficial effect. In one embodiment, the present invention relates to a method of treating an individual suffering from a disease or condition wherein inhibition of the GCS provides a benefit comprising administering a therapeutically effective amount of a compound of structural formula (I) to an individual in need thereof.

The compounds of structural formula (I) therefore can be used to treat a variety of diseases and conditions where inhibition of GCS provides a benefit. Examples of such diseases and condition include, but are not limited to, Tay-Sachs disease, type I, II, and III Gaucher disease, Sandhoff disease, and Fabry's disease; Parkinson's disease (J. R. Mazzulli et al., Cell 146:37-52, Jul. 8, 2011); type 2 diabetes; renal hypertrophy or hyperplasia associated with diabetic nephropathy; elevated plasma TNF-α; elevated blood glucose levels; elevated glycated hemoglobin levels; lupus; and a glomerular disease selected from the group consisting of mesangial proliferative glomerulonephritis, collapsing glomerulopathy, proliferative lupus nephritis, crescentic glomerulonephritis, and membranous nephropathy.

A compound of structural formula (I) also can be used to treat disorders involving cell growth and division, including cancer, collagen vascular diseases, atherosclerosis, and the renal hypertrophy of diabetic individuals (U.S. Pat. Nos. 6,916,802 and 5,849,326, each incorporated herein by reference); to inhibit the growth of arterial epithelial cells (U.S. Pat. Nos. 6,916,802 and 5,849,326, each incorporated herein by reference); to treat patients suffering from infections (M. Svensson et al., Infect. And Immun., 62:4404-4410 (1994)); to prevent a host, i.e., patient, from generating antibodies against the tumor (J. Inokuchi et al., Cancer Lett., 38:23-30 (1987); and to treat tumors (S. Hakomori Cancer Cells 3:461-470 (1991)); J. Inokuchi et al., Cancer Res., 50L6731-6737 (1990)); and (M. Ziche et al., Lab Invest., 67:711-715 (1992)). A compound of structural formula (I) further can be used to treat a polycystic kidney disease, including both autosomal dominant and recessive forms (T. A. Natoli et al., Nat. Med. 16:788-792 (2010)).

A method of the present invention can be accomplished by administering a compound of structural formula (I) as the neat compound or as a pharmaceutical composition. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of GCS provides a benefit, packaged separately or together, and an insert having instructions for using these active agents.

In many embodiments, a compound of structural formula (I) is administered in conjunction with a second therapeutic agent useful in the treatment of a disease or condition wherein inhibition of GCS provides a benefit. The second therapeutic agent is different from the compound of structural formula (I). A compound of structural formula (I) and the second therapeutic agent can be administered simultaneously or sequentially to achieve the desired effect. In addition, the compound of structural formula (I) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agents, for example, but not limited to, enzyme replacement therapy, gene therapy, and isofagamine.

In a method of treating type 2 diabetes, the second therapeutic agent can be one or more of insulin (e.g., NOVOLIN®, NOVOLOG®, VELOSULIN®); a sulfonylurea (e.g., DIABINESE®, GLUCOTROL®, GLUCOTROL XL®, DIABETA®, AMARYL®, ORINASE, TOLINASE®, MICRONASE, and GLYNASE®); metformin; an [alpha]-glucosidase inhibitor (e.g., GLYSET®); a thiazolidinedione (e.g., ACTOS® and AVANDIA®); nateglinide (STARLIX®); repaglinide (PRANDIN®), and combination drugs such as AVANDAMET® (AVANDIA® and metformin).

In a method of treating Parkinson's disease, the second therapeutic agent can be one or more of carbidopa/levodopa therapy; a dopamine agonist (apomorphine hydrochloride, bromocriptine, rotigotine, pramipexole, ropinirole, pergolide), an anticholinergic (benzotropine mesylate, trihexyphenidyl hydrochloride, procyclidine), an MAO-B inhibitor (selegiline, rasagiline), a COMT inhibitor (entacapone, tulcapone), and other medications including non-prescription, over-the-counter therapeutics (amantadine, rivastigmine tartrate, creatine, coenzyme Q10).

The diseases and conditions that can be treated in accordance to the invention include, for example, Gaucher disease, Fabry disease, Tay-Sachs disease, and diabetes. In particular, type II and type III Gaucher disease can be treated because compounds of structural formula (I) are capable of crossing the BBB. Prior GCS inhibitors either were incapable of crossing the BBB or had low potency and selectivity, and accordingly various diseases associated with glycolipid accumulation could not be treated.

In the present method, a therapeutically effective amount of one or more compound of structural formula (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the maximum tolerated dose (MTD) of a compound, defined as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the condition being treated, the length of time that activity is desired, and the age and the condition of the patient, and ultimately is determined by the attending physician. Dosage amounts and intervals can be adjusted individually to provide plasma levels of a compound of structural formula (I) that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a compound of structural formula (I) can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a GCS inhibitor of structural formula (I), or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, the compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the GCS inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

Prior GCS inhibitors possessed properties that hindered their development as therapeutic agents. In accordance with an important feature of the present invention, compounds of structural formula (I) were synthesized and evaluated as inhibitors for GCS, and, in particular, for having an ability to cross the BBB. The present GCS inhibitors are characterized by inhibition of GCS at low nanomolar concentrations, high specificity, and the absence of β-glucocerebrosidase binding.

REFERENCES

1. N. W. Barton et al., N Engl J Med 324, 1464-1470, (1991).
2. N. S. Radin, Glycoconj J 13, 153-157, (1996).
3. J. A. Shayman et al., Methods Enzymol 311, 373-387, (2000).
4. N. J. Weinreb et al., Am J Hematol 80, 223-229, (2005).
5. J. A. Shayman, Drugs of the Future 35, 613-621, (2010).
6. E. Lukina et al., Blood 116(20):4095-8, (2010).
7. A. Abe et al., J Clin Invest 105, 1563-1571, (2000).
8. Y. Liu et al., The Journal of clinical investigation 103, 497-505, (1999).
9. J. A. Shayman et al., Methods Enzymol 311, 42-49, (2000).
10. L. Shu et al., J Biol Chem 278, 31419-31425, (2003).
11. C. Shu et al., The Journal of pharmacology and experimental therapeutics 301, 820-829, (2002).
12. D. S. Wishart et al., Nucleic Acids Res 36, D901-906, (2008).
13. M. Jimbo et al., J Biochem-Tokyo 127, 485-491, (2000).
14. C. A. Lipinski et al., Advanced Drug Delivery Reviews 23, 3-25, (1997).
15. P. Garberg et al., Toxicol In Vitro 19, 299-334, (2005).
16. Q. Wang et al., Int J Pharm 288, 349-359, (2005).
17. K. M. Mahar Doan et al., The Journal of pharmacology and experimental therapeutics 303, 1029-1037, (2002).
18. P. D. Leeson et al., J Med Chem 47, 6338-6348 (2004).
19. H. Pajouhesh et al., NeuroRx 2, 541-553, (2005).
20. R. Cecchelli et al., Nat Rev Drug Discov 6, 650-661 (2007).
21. S. Lundquist et al., Pharm Res 19, 976-981 (2002).
22. U. Andersson et al., Biochemical pharmacology vol. 59, no. 7, pp. 821-829 (2000).
23. R. C. Baek et al., Neurochemistry international, vol. 52, no. 6, pp. 1125-1133 (2008).
24. R. C. Baek et al., Lipids, vol. 44, no. 3, pp. 197-205 (2009).
25. C. A. Denny et al., Journal of neuroscience research, vol. 83, no. 6, pp. 1028-1038 (2006).
26. C. A. Denny et al., Journal of neurochemistry, vol. 113, no. 6, pp. 1525-1535 (2010).
27. H. Galjaard, Annals of Clinical Biochemistry, vol. 16, no. 6, pp. 343-353 (1979).
28. E. C. Hauser et al., Biochemical genetics, vol. 42, no. 7-8, pp. 241-257 (2004).
29. M. Jeyakumar et al., Blood, vol. 97, no. 1, pp. 327-329 (2001).
30. M. Jeyakumar et al., Neuropathology and applied neurobiology, vol. 28, no. 5, pp. 343-357 (2002).
31. M. Jeyakumar et al., Brain: a journal of neurology, vol. 126, no. Pt 4, pp. 974-987 (2003).
32. J. L. Kasperzyk et al., Journal of neurochemistry, vol. 89, no. 3, pp. 645-653 (2004).
33. J. L. Kasperzyk et al., Journal of lipid research, vol. 46, no. 4, pp. 744-751 (2005).
34. T. Kolter et al., Biochimica et Biophysica Acta, vol. 1758, no. 12, pp. 2057-2079 (2006).
35. S. Kyrkanides et al., Journal of neuroimmunology, vol. 203, no. 1, pp. 50-57 (2008).

36. L. J. Macala et al., Journal of lipid research, vol. 24, no. 9, pp. 1243-1250 (1983).
37. D. Phaneuf et al., Human molecular genetics, vol. 5, no. 1, pp. 1-14 (1996).
38. K. Sango et al., Nature genetics, vol. 11, no. 2, pp. 170-176 (1995).
39. T. N. Seyfried et al., Biochemical genetics, vol. 17, no. 1-2, pp. 43-55 (1979).
40. T. N. Seyfried et al., Biochemical genetics, vol. 18, no. 11-12, pp. 1229-1237 (1980).

What is claimed:

1. A compound having a structure wherein $R^1$ and $R^2$, independently, are H, $C_{1-4}$alkyl, $OC_{1-4}$alkyl, $C_{3-6}$cycloalkyl, or $OC_{3-6}$cycloalkyl, each optionally substituted with one or more F, wherein one carbon of a cycloalkyl group optionally is replaced by O, or $R^1$ and $R^2$ can be taken together to form an $OCH_2CH_2O$ ring with either carbon atom substituted by one or two $CH_3$;

$NR^5R^{5'}$ is selected from the group consisting of 1-pyrrolidinyl, 3-fluoro-1-pyrrolidinyl, and 1-azetidinyl;

$R^3$ is H or F;

G is $CH_2$ or O;

$R^4$ is H or $CH_3$;

$R^6$ is H, $C_{1-3}$alkyl, $C_{3-6}$cycloalkyl, or $CD_3$; and $R^7$ and $R^8$, independently, are H, F, or $OC_{1-3}$alkyl, or a pharmaceutically acceptable salt thereof.

2. The compound of claim 1 wherein $R^1$ is —H, —OC($CH_3$)$_3$, —OCH$_3$, —OCF$_3$, —OCHF$_2$, 3. The compound of claim 1 wherein $R^1$ is H.
4. The compound of claim 1 wherein $R^2$ is H.
5. The compound of claim 1 wherein $R^1$ and $R^2$ are taken together to form 6. The compound of claim 1 wherein $R^3$ is H or F.
7. The compound of claim 1 wherein $R^4$ is H or $CH_3$.

8. The compound of claim 1 wherein —$NR^5R^{5'}$ is

9. The compound claim 1 wherein each of $R^1$, $R^2$, $R^7$, and $R^8$ is —H.

10. The compound of claim 1 wherein $R^7$ is H and $R^8$ is $OCH_3$, or $R^7$ is $OCH_3$ and $R^8$ is H, or $R^7$ is H and $R^8$ is H.

11. The compound of claim 1 wherein is

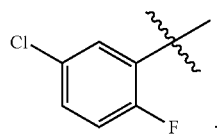
12. A compound selected from the group consisting of
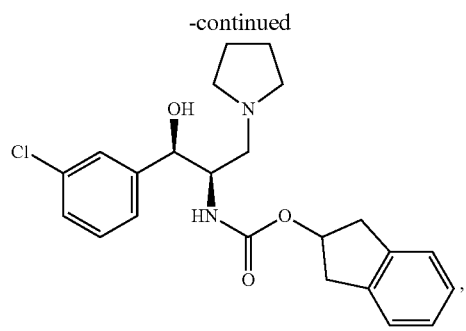
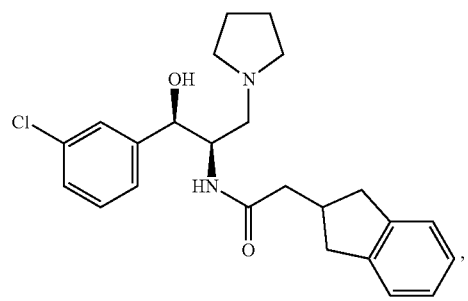
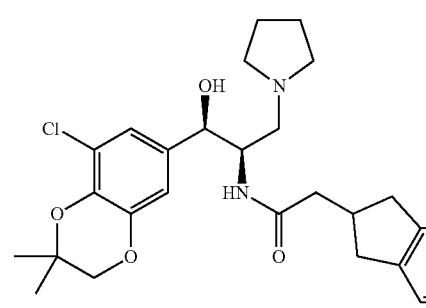
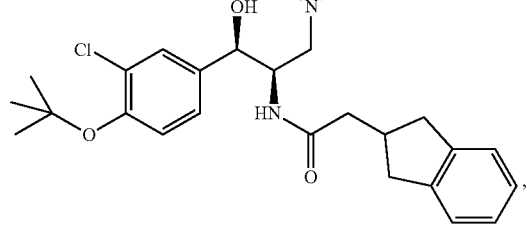
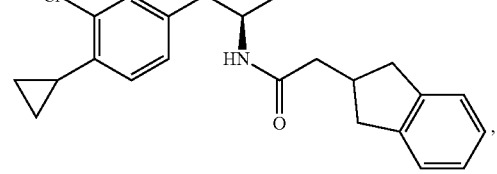
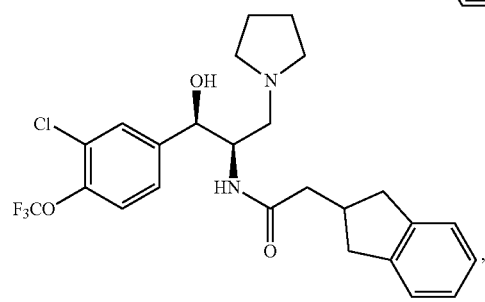
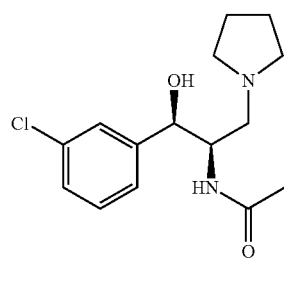
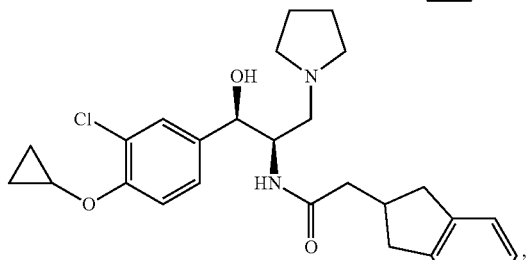
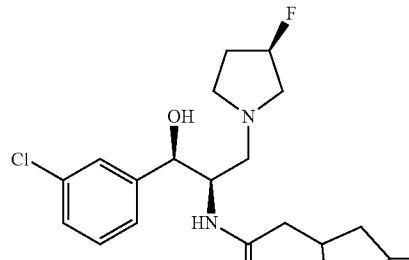
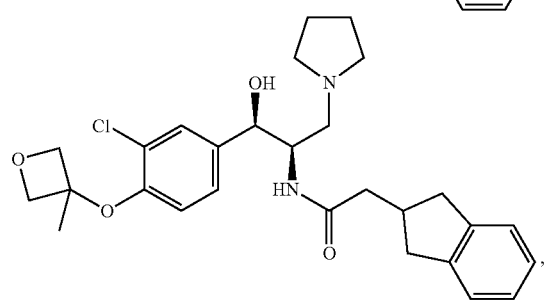
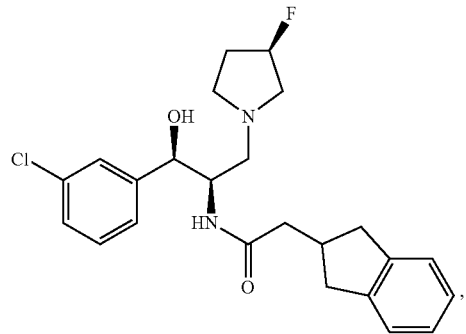

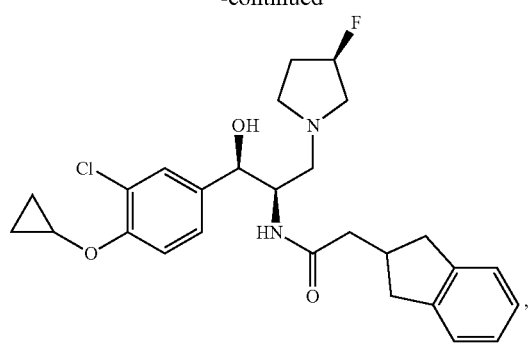,
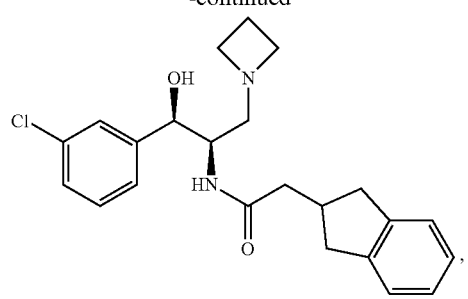,
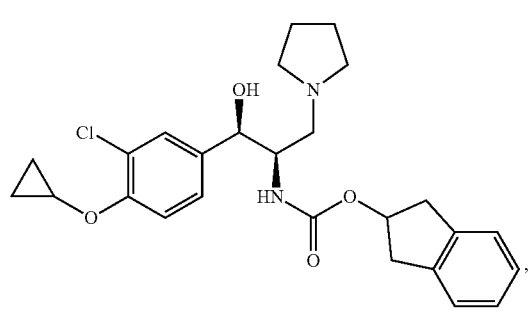,
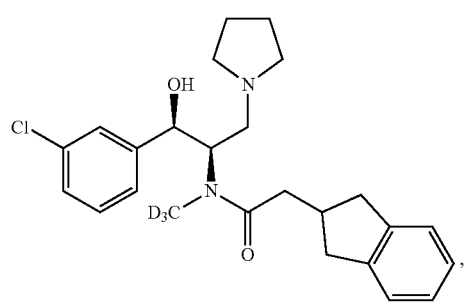,
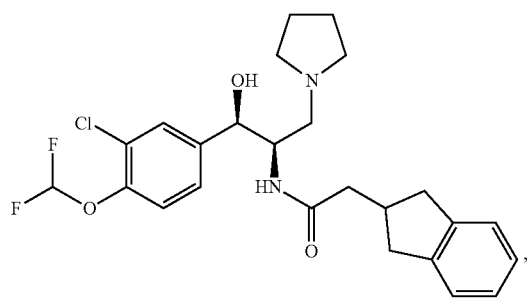,
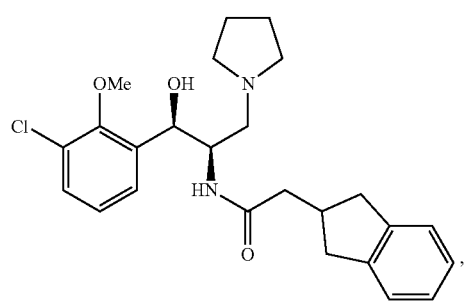,
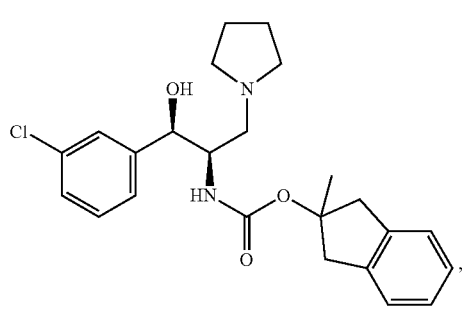,
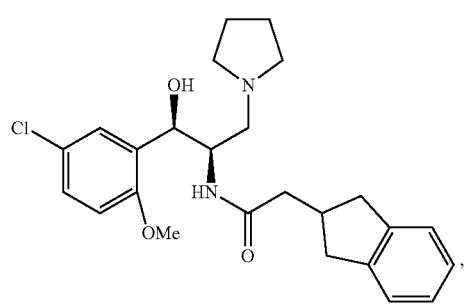,
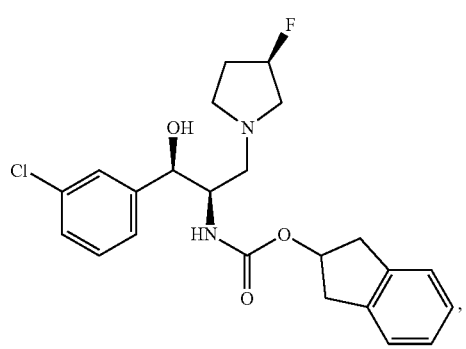,
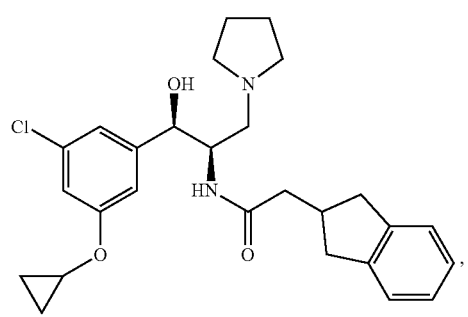,

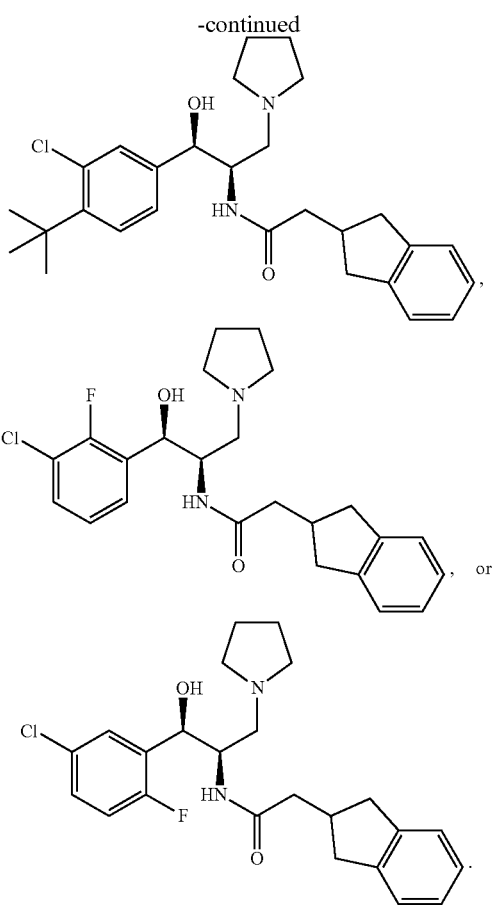

13. A pharmaceutical composition comprising a compound of claim 1 and a pharmaceutically acceptable carrier or vehicle.

14. A method of treating a disease or condition wherein inhibition of GCS provides a benefit comprising administering a therapeutically effective amount of a compound of claim 1 to an individual in need thereof.

15. The method of claim 14 wherein the disease or condition is a Gaucher disease, Fabry disease, Sandhoff disease, Tay-Sachs disease, Parkinson's disease, multiple myeloma, ADPCD, type 2 diabetes, hypertrophy or hyperplasia associated with diabetic neuropathy, an elevated plasma TNF-α level, an elevated blood glucose level, an elevated glycated hemoglobin level, a glomerular disease, or lupus.

16. The method of claim 15 wherein the Gaucher disease is type I, type II, or type III Gaucher disease.

17. The method of claim 15 wherein the glomerular disease is selected from the group consisting of mesangial proliferative glomerulonephritis, collapsing glomerulopathy, proliferative lupus nephritis, crescentic glomerulonephritis, and membranous nephropathy.

18. The method of claim 14 wherein the disease or condition is a disorder involving cell growth, a disorder involving cell division, a collagen vascular disease, atherosclerosis, renal hypertrophy in a diabetic individual, a growth of arterial epithelial cells, an infection, a tumor, and a polycystic kidney disease.

19. The method of claim 18 wherein the disease or condition is a cancer or an autosomal dominant or recessive form of the polycystic kidney disease.

20. A method of inhibiting glucosylceramide synthase or lowering a glycosphingolipid concentration in an individual in need thereof comprising administering a therapeutically effective amount of a compound of claim 1 to the individual.

* * * * *